United States Patent
Pace-Asciak

(10) Patent No.: US 8,071,654 B2
(45) Date of Patent: Dec. 6, 2011

(54) INHIBITORS OF THROMBOXANE FORMATION AND ACTION

(76) Inventor: Cecil R. Pace-Asciak, Toronto (CA)

( * ) Notice: Subject to any disclaimer, the term of this patent is extended or adjusted under 35 U.S.C. 154(b) by 1543 days.

(21) Appl. No.: 10/416,132

(22) PCT Filed: Nov. 9, 2001

(86) PCT No.: PCT/CA01/01607
§ 371 (c)(1),
(2), (4) Date: Feb. 27, 2004

(87) PCT Pub. No.: WO02/38157
PCT Pub. Date: May 16, 2002

(65) Prior Publication Data
US 2004/0132705 A1    Jul. 8, 2004

Related U.S. Application Data

(60) Provisional application No. 60/246,744, filed on Nov. 9, 2000, provisional application No. 60/299,752, filed on Jun. 22, 2001.

(51) Int. Cl.
*A01N 31/00* (2006.01)
*A61K 31/045* (2006.01)
(52) U.S. Cl. .......................................... 514/738
(58) Field of Classification Search ............... 514/183, 514/738
See application file for complete search history.

(56) References Cited

U.S. PATENT DOCUMENTS

| | | | | |
|---|---|---|---|---|
| 5,616,607 A | * | 4/1997 | Pace-Asciak et al. | 514/430 |
| 5,783,564 A | * | 7/1998 | Chaki et al. | 514/42 |
| 6,093,741 A | | 7/2000 | Gosselin et al. | |
| 6,391,305 B1 | | 5/2002 | Feng et al. | |
| 6,673,785 B1 | * | 1/2004 | Pace-Asciak | 514/183 |

FOREIGN PATENT DOCUMENTS

| | | |
|---|---|---|
| CA | 2159584 | 10/1994 |
| CA | 2159584 A1 | 10/1994 |
| WO | 94/22848 | 10/1994 |
| WO | WO 94/22848 | 10/1994 |
| WO | 97/29751 | 8/1997 |
| WO | 99/59578 | 11/1999 |
| WO | 00/07589 | 2/2000 |
| WO | 01/10422 A2 | 2/2001 |
| WO | 03/099285 A1 | 12/2003 |

OTHER PUBLICATIONS

Fink, Mitchell P. "Therapeutic options directed against platelet activating factor, eicosanoids and bradykinin in sepsis". Journal of Antimicrobial Chemotherapy. 1998. vol. 41, Suppl. A. pp. 81-94.*
Mitchell et al. "Cyclo-oxygenase-2: pharmacology, phycology, biochemistry and relevance to NSAID therapy". British Journal of Pharmacology. 1999. vol. 128. pp. 1121-1132.*

(Continued)

*Primary Examiner* — Gollamudi Kishore
*Assistant Examiner* — Benjamin Packard
(74) *Attorney, Agent, or Firm* — Dinsmore & Shohl LLP

(57) ABSTRACT

Methods and compositions employing as active ingredient hepoxilins and hepoxilin analog useful for inhibiting thromboxane formation and antagonizing thromboxane activity. Methods and compositions employing these compounds provide treatment for a number of disease conditions.

24 Claims, 14 Drawing Sheets

OTHER PUBLICATIONS

Reynaud et al. "Hepoxilin A3 Formation in the Rat Pineal Gland Selectively Utilizes (12S)-Hydroperoxyeicosatetraenoic Acid (HPETE), but Not (12R)-HPETE". The Journal of Biological Chemistry. 1994. vol. 269, No. 39. pp. 23976-23980.*
Brune et al (Journal of Biological Chemistry, 266:29 (1991) 19232).*
Hamberg, M. et al., (1975), Thromboxanes: A new group of biologically active compounds derived from prostaglandin endoperoxides, Proc. Natl. Acad. Sci. USA, v. 72, pp. 2994-2998.
Hamberg, M. et al., (1974), Prostaglandin Endoperoxides. Novel Transformations of Arachidonic Acid in Human Platelets Oric, Batk, Acad. Sci. USA, v. 71, pp. 3400-3404.
Diczfalusy, U. et al., (1980), Enzymatic Conversion of $C_{21}$ Endoperoxides to Thromboxanes and hydroxy acids Biochem. Biophys. Res. Commun., v. 94, pp. 1417-1423.
Hammarstrom, S. et al., (1998), Biosynthesis of Thromboxanes, Advances in Prostaglandin and Thromboxane Research, v. 6, pp. 267-274.
Fu, Z.Z. et al., (1992), Thromboxane/prostacyclin Balance in Type II Diabetes: Gliclazide Effects, Metabolism, v. 41, pp. 33-35.
Hendra, T. et al., (1989), Platelet Function, Platelet Prostanoids and Vascular Prostacyclin in Diabetes mellitus, Prostagl. Leuk. Essen. Fatty Acids., v. 35, pp. 197-212.
Webster, J. et al., (1981), Plasma Levels of 6-Oxo-PGF$_{1\alpha}$., the Hydrolysis Product of Prostacyclin, May Be Reduced in Diabetes, Clin. Pharmacol. Prostacyclin, pp. 113-115.
Fitzgerald, D. J. et al., (1990), Thromboxane $A_2$ synthesis in pregnancy-induced hypertension, Lancet, v. 335, pp. 751-754.
Himmelstein, S. I., et al., (1989), The role of thromboxane in two-kidney, one-clip Goldblatt hypertension in rats, Am. J. Physiol., v. 257, pp. 190-196.
Lüscher, T. F. (1990, Imbalance of Endothelium-derived Relaxaing and Contracting Factors, Am. J. Hypertens., v. 3, pp. 317-330.
Minuz, P. et al., (1990), Prostacyclin and Thromboxane Biosynthesis in Mild Essential Hypertension, Hypertension, v. 15, pp. 469-474.
Purkerson, M. Martin et al., (1985), Inhibitors of Thromboxane Synthesis and Ameliorate the Development of Hypertension in Wistar Rats with spontaneous Hypertension (SHR), Meeting of the American Society of Nephrology, Washington, D.C. USA.
Yamashita, W. et al., (1986), A Thromboxane Synthetase Antagonist Has Beneficial Effect on Renal Function in Nephritis With Hypertention, Forty-third Annual National Meeting of The American Federation for Clinical Research Washington, D.C. USA.
Fiedler, V. B. et al., (1989), Reduction of in vivo Coronary Artery Thrombosis by the Novel Thromboxane Antagonist (3R)-3-(4-Fluorophenylsulfonamido)-1,2,3,4-tetrandro-9-carbozolepropanoic Acid, Arzneimittelforschung, v. 39, pp. 1527-1530.
Parellada, P. P. et al., (1977), Action of Selective Inhibitor of Thromboxane Synthetase on Experimental Thrombosis Induced by Arachidonic Acid in Rabbits, Lancet, p. 40.
Randall, M. J. et al., (1982), Acute Arterial Thrombosis in Rabbits: Reduced Platelet Accumulation After Treatment With Thromboxane Synthetase Inhibitor Dazoxiben Hydrochloride, (UK-37, 24801), Thromb. Res. v. 28, pp. 607-616.
Silver, R. M. et al., (1995), Bacterial Lipopolysaccharide-mediated Fetal Death, J. Clin. Invest., v. 95, pp. 725-731.
Zaitsu, M. et al., (1999), Induction of cytosolic phospholipase $A_2$ and prostaglandin $H_2$ synthase-2 by lipopolysaccharide in human polymorphonuclear leukocytes, Eur. J. Haematol., v. 63, pp. 94-102.
Wolkow, P. P. et al., (1997) Pneumotoxicity of Lipopolysaccharide I Nitric Oxide Deficient Rats Is Limited by a Thromboxane Synthase Inhibitor, J. Physiol. Pharmacol., v. 48, pp. 645-653.
Coleman, R. A. et al., (1981), Comparison of the Actions of U-46619, Prostaglandin $H_2$-Analogue, With Those of Prostaglandin $H_2$ and Thromboxane $A_2$ on Some Isolated Smooth Muscle Preparations, J. Pharmacol., v. 73, pp. 773-778.
Pollock, W. K., (1984) Thromboxane-induced phosphatidate formation in human platelets, Biochem., J. v. 219, pp. 833-842.
Tymkewycz, P. M. et al., (1991) Heterogeneity of thromboxane $A_2$ (TP-) receptors: evidence from antagonist but not agonist potency measurements, Br. J. Pharmacol., v. 102, pp. 607-614.
Heidemann, S. M. et al., (1997), Protective effects of a thromboxane synthetase inhibitor and continuous arteriovenous hemofiltration in rat endotoxic shock, Prostagl. Leuk. Essen. Fatty Acids, v. 56, pp. 473-478.
Kamilo, T. et al., (1993) An Improved and Convenient Procedure for the Synthesis of 1-Substituted Imidazoles, Chem. Pharm. Bull. (Tokyo), v. 31, pp. 1213-1221.
Pace-Asciak, C. R. et al., (1999), The Hepoxilins, Lipoxygenases and Their Metabolites- Biological Functions. Advances in Experimental Medicine and Biology, v. 447, Eds. S. Nigam and C.R. Pace-Asciak, Kluwer Academic/Plenum Publishers, New York, pp. 123-132.
Pace-Asciak, C. R. (1994), Hepoxilins: a review on their cellular actions, Biochim Biophys. Acta, v. 1215, pp. 1-8.
Pace-Asciak, C. R. et al., (1995), Hepoxilins: A Review on Their Enymatic Formation, Metabolism and Chemical Synthesis, Lipids, v. 30, pp. 107-114.
Laneuville, O. Reynaud et al., (1993), Hepoxilin $A_3$ inhibits the rise in free intracellular calcium evoked by formyl-methionyl-leucyl-phenylalanine, platelet-activating factor and leukotriene $B_4$ Biochem J., v. 295, pp. 393-397.
Dho, s. et al., (1990), Hepoxilin $A_3$ induces changes in cytosolic calcium, intracellular pH and membrane potential in human neutrophils, Biochem. J., v. 266, pp. 63-68.
Reynaud, D. et al., (1996), Hepoxilin $A_3$-specific binding in human neutrophils, Biochem. J., v. 313, pp. 537-541.
Margalit, A. et al., Hepoxilin $A_3$ is the endogenous lipid mediator opposing hypotonic swellin g of intact human platelets, Proc. Natl. Acad. Sci. (USA), v. 90, pp. 2589-2592.
Belardetti, F. et al., (1988), Up-and down-modulation of single K$^+$channel function by distinct second messengers, TINS, v. 11, pp. 232-238.
Belardetti, F. et al., (1989), Products of Heme-Catalyzed Transformation of the Arachidonate Derivative 12-HPETE Open S-Type K$^+$Channels in Aplysia, Neuron, v. 3, pp. 497-505.
Urban, M. (2002), COX-2 Specific Inhibitors Offer Improved Advantages Over Traditional NSAIDs, Orthopedics, v. 23, pp. 761-764.
Everts et al., (2000), COX-2-Specific Inhibitors-the Emergence of a New Class of Analgesic and Anti-inflammatory Drugs, Clin. Rheumatol., v. 19, pp. 331-343.
Margalit et al., (1994), Endogenous hepoxilin $A_3$, produced under short duration of high shear-stress, inhibits thrombin-induced aggregation in human platelets Biochim. Biophys. Acta, v. 1190, pp. 173-176.
Gilutz, H., (1997), Deactivation Mechanism of Platelets, Endothelium, v. 5, pp. 137-138.
Margalit et al., (1995), Low Regulatory Volume Decrease Rate in Platelets from Ischemic Patients: A Possible Role for Hepoxilin $A_3$ in Thrombogenicity, Platelets (Edinburg), Churchill Livingstone Medical Journals, GB, v. 6, pp. 371-376.
Pace-Asciak, C. R. (1999), Hepoxilin raise circulating insulin levels in vivo, FEBS Letters, v. 461, pp. 165-168.
Laneuville et al., (1992), Hepoxilins sensitize blood vessels to noradrenaline—stereospecificity of action, J. Pharmacol., v. 105, pp. 297-304.
Fang et al., (1996), Functional Implications of a Newly Characterized Pathway of 11,12-Epoxyeicosatrienoic Acid Metabolism in Arterial Smooth Muscle, Circulation Research, v. 79, pp. 784-793.
Canadian Application No. 2,427,774 Office Action dated Apr. 16, 2010.
Pace-Asciak et al., "Hepoxilins", General Pharmac, vol. 24, No. 4, pp. 805-810, 1993.
Pace-Asciak et al., "Hepoxilins Modulate Second Messenger Systems in the Human Neuthrophil", Cell-Cell Interactions in the Release of Inflammatory Mediators, pp. 133-139, 1991.
Pace-Asciak et al., "Hepoxilins, Potential Endogenous Mediators of Insulin Release", Prog. Lipid Res., vol. 25, pp. 625-628, 1986.
Pace-Asciak et al., "Hepoxilins raise circulating insulin levels in vivo", FEBS Letters 461, pp. 165-168, 1999.
Pace-Asciak et al., Arachidonic Acid Epoxides, "Isolation and Structure of Two Hydroxy Epoxide Intermediates in the Formation of 8,11,12- and 10,11,12-Trihydroxyeicosatrienoic Acids", The Journal of Biological Chemistry, vol. 258, No. 11, Issue of Jun. 10, pp. 6835-6840, 1983.

Pace-Asciak et al., "Oxygenation of Arachidonic Acid into 8,11,12- and 10,11,12-Trihydroxyeicosatrienoic Acid by Rat Lung", Advances in Prostaglandin, Thromboxane, and Leukotriene Research, vol. 11, pp. 133-139.

Pace-Asciak et al., "Resolution by AEAE-Cellulose Chromatrography of the Enzymatic Steps in the Transofrmation of Archidonic Acid into 8,11,12- and 10-11,12-Trihydroxy-Eicosatrienoic Acid by the Rat Lung", Prostaglandins, vol. 25, No. 1, Jan. 1983.

Pace-Asciak et al., "The Hepoxilins—A Review", Lipoxygenases and Their Metabolites, pp. 123-132, 1999.

Pace-Asciak et al., "The red wine phenolics trans-resveratrol and quercetin block human platelet aggretation and eicosanoid synthesis: Implications for protection against coronary heart disease", Elsevier Science, Clinica Chimica Acta 235, pp. 207-219, 1995.

Prost et al., "Evaluation of the Antimicrobial Activities of Plant Oxylipins Supports Their Involvement in Defense against Pathogens", Plant Physiology, vol. 139, pp. 1902-1913, Dec. 2005.

Qiao et al., "The Hepoxilin Analog PBT-3 Induces Apoptosis in BCR-ABL-positive K562 Leukemia Cells", Anticancer Research 23, pp. 3617-3622, 2003.

Quieroz et al., "Determination of the Absolute Configuration of 6-Alkylated a-Proones from Ravensara Crassifolia by LC-NMR", Phytochemical Analysis 14, pp. 34-39, 2003.

Rajaratnam et al., "Ilmtinib for chronic myeloid leukemia: a NICE mess", The Lancet, vol. 358, Dec. 1, 2001.

Reynaud et al., "Novel Platelet Antiaggregating Substances", Biomedical and Biophysical Research Communciations 284, pp. 580-582, 2001.

Rumi et al., "Can PPARy Ligands Be Used in Cancer Therapy?", Curr. Med. Chem. Anti Cancer Agents 4, pp. 465-477, 2004.

Sawyers, "Cancer Treatment in the STI571 Era: What will Change?", Journal of Clinical Oncology, vol. 19, No. 18s (Sep. 15 Supplement), pp. 13s-26s, 2001.

Seppa, "Leukemia overpowers drug in two ways", Science News, vol. 159, pp. 389, Jun. 23, 2001.

Shimizu et al., "Archidonic Acid Cascade and Signal Transduction", Journal of Neuochemistry, 1990.

Spiegelman, "PPAR-y: Adipogenic Regulator and Thiazolidinedione Receptor", Diabetes, vol. 47, Apr. 1998.

Sun Lumin et al., "Palladium Mediated Allylic Mitsunobu Displacement: Sterocontrolled Synthesis of Hepoxilin A3 and Trioxilin A3 Methyl Esters", Tetrahedron Letters, vol. 33, No. 16, pp. 2091-2094, 1992.

Tan et al., "Peroxisome Proliferator-Activated Receptor (PPAR)-B as a Target for Wound Healing Drugs—What is Possible?", Am J Clin Dermotol 4 (8), pp. 523-530, 2003.

Tontonoz et al., "mPPARy2: tissue-specific regulator of an adipocyte enhancer", Genes and Development 8, pp. 1224-1234, 1994.

Wang et al., "Steroselective actions of hepoxilins A3 and B3 and their cyclopropane analogs . . . on bradykinin and PAF-evoked potentiation of vascular leakage in rat skin"m General Pharmacology, Teh Vascular System, General Pharmacology 33, pp. 377-382, 1999.

Weisberg et al., "Mechanism of resistance to the ABL tyrosine kinase inhibitor STI571 in BCR/ABL-transformed hematopoietic cell lines", Bllod, vol. 95, No. 11, Jun. 2000.

Alali et al., "(2,4-cis and trans)-Ggantecinone and 4-Deoxygigantecin, Bioactive Nonadjacent Bis-Tetrahydrofuran Annonaceous Acetogenins, from Goniothalamus giganteus", American Chemical Society and American of Pharmacognosy, J. Nat. Prod., 60, pp. 929-933, Apr. 21, 1997.

Anton et al., "Occurrence of Hepoxilins and Trioxilins in Psoriatic Lesions", The Society for Investigative Dermotology, Inc., 1998.

Arndt et al, "Liposomal Bleomycin: Increased Therapeutic Activity and Decreased Pulmonary Toxicity in Mice", Taylor & Francis, 2001.

Chawla et al., "Peroxisome proliferator and retinoid signaling pathways co-regulate preadipocyte phenotype and survival", Proc. Natl. Acad. Sci, USA, vol. 91, pp. 1786-1790, Mar. 1994.

Chen et al., "A transcriptional co-repressor that interacts with nuclear hormone receptors", Letters to Nature, Sep. 15, 1995.

Cheng, "Dramatic Results in Trial of New Lukemia Drug", International Medical News Group, 2000.

Corey et al., "Total Synthesis of 12-(S)-10-Hydroxy-Trans-11, 12-Epoxyeicosa-5, 9, 14-(Z)-Trienoic Acids, Metabolites of Arachidonic Acid in Mammallian Blood Platelets", Tetrahedron Letters, vol. 24, No. 45, pp. 4913-4916, 1983.

Demin et al., Chemical Abstract, vol. 113, 1990.

Demin et al., Chemical Abstract, vol. 114, 1991.

Demin et al., "Chemical synthesis and actions of 11, 12-thiirano-hepoxilin A3", Journal of Lipid Mediators and Cell Signaling, 13, pp. 63-72, 1996.

Demin et al., "Extractive Derivatization of the 12-Lipoxygenase Products, Hepoxilins, and Related Compounds into Fluorescent Anthryl Esters for Their Complete High-Performance Liquid Chromatography Profiling in Biological Systems", Analytical Biochemistry 226, pp. 252-255, 1995.

Demin et al, "High-Performance liquid chromatographic separation of fluorescent esters of hepoxilin enantiomers on a chiral stationary phase", Journal of Chromatography B, 672, pp. 282-289, 1995.

Demin et al., "Synthesis of Racemic 11, 12-Cyclopropyl Analogs of Hepoxilins A3 and B3", Tetrahedron Letters, vol. 34, No. 27, pp. 4305-4308, 1993.

Dias et al., "Antisense Oligonucleotides: Basic Concepts and Mechanisms", Molecular Cancer Therapeutics, vol. 1, pp. 347-355, Mar. 2002.

Fernandes et al., Asymmetric dihydroxylation and one-pot epoxidation routes to (+)- and (−)-posticlure: a novel trans-expoxide as a sex pherome component of *Orgyia postica* (Walker), Tetrahedron 58, pp. 6685-6690, 2002.

Goodman & Gilman's, "Teh Pharmacological Basis of Therapeutics" Tenth Edition, 2001.

Gorman et al., "Inhibition of human platelet thromboxane synthetase by 9, 11-azoprosta-5, 13-dienoic acid", Proc. Natl. Acad. Sci USA, vol. 74, No. 9, pp. 4007-4011, Sep. 1977.

Grinstein et al., "Amiloride-Sensitive Na+/H+ Exchange in Human Neutrophilis: Mechanism of Activation by Chemotactic Factors", Biochemical and Biophysical Research Communications, vol. 122, No. 2, pp. 755-762, Jul. 31, 1984.

Hallett et al., "Direct measurement of intracellular free CA2+ in rat peritoneal macrophages: correlation with oxygen-radical production", Immunology, 50, pp. 487-495, Jun. 6, 1983.

Helledie et al., "Lipid-binding proteins modulate ligand-dependent trans-activation by peroxisome proliferator-activated receptors and localize to the nucleus as well as the cytoplasm", Journal of Lipid Research, vol. 41, pp. 1740-1751, 2000.

Hishinuma et al., "Troglitazone has a reducing effect on thromboxane production", Prostaglandins and other Lipid Medicators 62, pp. 135-143, 2000.

Jaconi et al., "The Regulation of Store-dependent CA2+ Influx in HL-60 Granulocytes Involves GTP-sensitive Elements", The Journal of Biological Chemistry, vol. 258, No. 35, pp. 26075-26078, Issue of Dec. 15, 1993.

Jankov et al., "Hepoxilin Analogs Inhibit Blemycin-Induced Pulmonary Fibrosis in the Mouse", The Journal of Pharmacology and Experimental Therapeutics, vol. 301, No. 2, pp. 435-440, Jan. 29, 2002.

Kliewer et al., "A Prostaglandin J2 Metabolite Binds Peroxisome Proliferator-Activated Receptor y and Promotes Adipocyte Differentiation", Cell Press, vol. 83, pp. 813-819, Dec. 1, 1995.

Kopelovich et al., "Peroxisome Proliferator-activated Receptor Modulators As Potential Chemopreventive Agents", Molecular Cancer Therapeutics, vol. 1, pp. 357-363, Mar. 2002.

Laneuville et al., "Hepoxilin A3 increases vascular permeability in the rat skin", Eicosanoids Springer-Verlag, pp. 95-97, 1991.

Laneuville et al., "Hepoxilin A3 inhibits the rise in free intracelular calcium evoked by formyl-methionyl-leucyl-phenylalanine, platelet-activating factor and leukotriene B4", Biochem. J. 295, pp. 393-397, 1993.

Lapitskaya et al., "A Chemoselective Synthesis of Functionalized 1, 4-Alkadiynes (skipped Diacetylenes)", Synthesis, No. 1, Jan. 1993.

Lehmann et al., "An Antidiabetic Thiazolidinedione is a High Affinity Ligand for Peroxisome Proliferator-activated Receptor y (PPARy)", The Journal of Biological Chemistry, vol. 270, No. 22, pp. 12953-12956, Issue of Jun. 2, 1995.

Li et al., "The Hepoxililn Analog, PTB-3, Inhibits Growth of K-562 CML Solid Tumours In Vivo in Nude Mice", In vivo 19, pp. 1985-190, 2005.

Lim et al., "Imatnib for Chronic Myelogeous Leukemia a NICE Mess", The Lancet, vol. 358, Dec. 1, 2001.

Lozzio et al., "Human chronic myelogenous leukemia cell-line with positive Philadelphia chromosome", Teh American Society of Hematology, Blood Journal, pp. 321-334, May 8, 2009.

Majumdar et al., "Catalytic Asymmetric and Steroselective Synthesis of Vinylcyclopropanes", Synlett, No. 3, Apr. 3, 2002, ISSN 0936-5214, pp. 423-426.

Martin et al., "Induction of Apoptosis (Programmed Cell Death) in Human Leukemic HL-60 Cells by Inhibition of RNA or Protein Synthesis", The Journal of Immunology, vol. 145, No. 6, pp. 1859-1867, Sep. 15, 1990.

Mauro et al., "STI571: A Paradigm of New Agents for Cancer Therapeutics", Journal of Clinical Oncology, vol. 20, No. 1, pp. 325-334, Jan. 1, 2002.

McWhirter et al., "Activation of Tyrosine Kinase and Microfilament-Binding Functions of c-abl by bcr Sequences in bcr/abl Fusion Proteins", American Society for Microbiology, Molecular and Cellular Biology, vol. 11, No. 3, pp. 1553-1565, Mar. 1991.

"The Merck Manual of Diagnosis and Therapy", 17th Edition, pp. 973-995, 1999.

Moghaddam et al., "Discovery of the Mammalian Insulin Release Modulator, Hepoxilin B3, from the Tropical Red Algae *Platysiphonia miniata* and *Cottoniella filamentosa*", The Journal of Biolocal Chemistry, vol. 265, No. 11, Issue of Apr. 15, pp. 6126-6230, 1990.

O'Brien, "Imtinib for chronic myeloid leukemia: a NICE mess", The Lancet, vol. 358, Dec. 1, 2001.

Omar et al., "Asymmetric Sharpless epoxidation of 13S-hydroxy-9Z 11E-ocadecadienoic acid (13S-HODE)", Eur. J. Lipid Sci. Thecnol. 105, pp. 43-44, 2003.

Pace-Asciak et al., "Adv. Prostagl. and Leuk. Res.", 11th International Conference, Florence, Italy, Jun. 4-8, 2000, Abstract pp. 18.

Pace-Asciak et al., "A glutathione conjugate of hepoxilin A3: Formation and action in the rat central nervous system", Proc Natl. Acad. Sci., vol. 87, pp. 3037-3041, Apr. 1990.

Pace-Asciak et al., "A New Family of Thromboxane Receptor Antagonists with Secondary Thromboxane Synthase Inhibition", The Journal of Pharmacology and Experimental Therapeutics, vol. 301, No. 2, pp. 618-624, Jan. 2002.

Pace-Asciak et al., "Chemical Abstract", vol. 105, 1986.

Pace-Asciak et al., "Arachidonic Acid Epoxides", The Journal of Biological Chemistry, vol. 259, No. 13, Issue of Jul. 10, pp. 8332-8337, 1984.

Pace-Asciak et al., "Epoxide hydratase assay in human platelets using hepoxilin A3 as a lipid substrate", Biochemica Acta 875, pp. 406-409, 1986.

Pace-Asciak, "Hemoglobin- and Hemin-Catalyzed Transformation of 12L-Hydroperoxy-5,8,10,14-Eicosatetraenoic Acid", Biochimica at Biophysica Acta, 793, pp. 485-488, 1984.

Pace-Asciak et al., "Hepoxilin, A New Family of Insulin Secretagogues Formed by Intact Rat Pancreatic Islets", Prostaglandins Leukotrienes and Medicine 16, pp. 173-180, 1984.

Pace-Asciak et al., "Hepoxilin Analogs Inhibit Blemycin-Induced Pulmonary Fibrosis in the Mouse", The Journal of Pharmacology and Experimental Therapeutics, vol. 301, No. 2, pp. 435-440, Jan. 29, 2002.

Pace-Asciak et al., "Hepoxilin Analogs, Potential New Therapeutics in Disease", Current Pharmaceutical Design, 12, pp. 963-969, 2006.

\* cited by examiner 1  collagen (2 μg)
2  U46619 (10 ng)
3  ASA (20 μg) + collagen (2 μg) + U46619 (10 ng)
4  ASA (20 μg) + collagen (2 μg) + PBT-3 (1 μg) + U46619 (10 ng)

INHIBITORS OF THROMBOXANE FORMATION AND ACTION

RELATED APPLICATIONS

The present application claims priority under 35 U.S.C. §119 of U.S. Application Ser. Nos. 60/246,744 filed Nov. 9, 2000 and 60/299,752 filed Jun. 22, 2001.

FIELD OF THE INVENTION

The present invention relates to therapeutic methods and pharmaceutical compositions employing compounds which inhibit thromboxane formation and antagonise thromboxane activity.

BACKGROUND OF THE INVENTION

The maintenance of normal vascular tone in mammals involves a homeostatic balance between factors which promote vasodilation and factors which promote vasoconstriction. Thromboxane $A_2$ ($TxA_2$), for example, is a powerful vasoconstrictor (1) and also a potent mediator of platelet aggregation (14). Prostaglandins such as prostaglandin $E_2$ and prostacyclin, on the other hand, have vasodilatory and anti-platelet aggregation effects.

Many diseases involve a perturbation of this normal homeostatic balance. For example, diabetes mellitus (5-7), hypertension (8-13), thrombosis (14-16) and septic shock (17-19) are associated with an imbalance of the thromboxane: prostacyclin or thromboxane: prostaglandin $E_2$ ratios in favour of thromboxane. There is therefore considerable interest in finding ways of selectively controlling thromboxane formation, so as to block the vasoconstrictor and aggregatory component of the prostaglandin system (thromboxane) without affecting the vasodilator and anti-aggregatory prostaglandins.

Prostaglandins, including thromboxane, are formed from a common precursor, $PGH_2$. This precursor is formed through the action of cyclooxygenase (COX) and is transformed by specific enzymes into each of the prostaglandins and thromboxane. Platelets convert $PGH_2$ selectively into thromboxane $A_2$ through the action of the $PGH_2$ metabolizing enzyme, thromboxane $A_2$ synthase. In other tissues and cells, $PGH_2$ is converted into other prostaglandin types, e.g. prostaglandin $E_2$ and $I_2$. Since thromboxane $A_2$ ($TxA_2$) has a very short half life in the body (30 sec), stable analogs of $TxA_2$ which mimic its actions have been explored; two such analogs are U44609 (20, 21) and U46619 (22). These analogs cause actions similar to $TxA_2$, i.e. they cause platelet shape change and aggregation, as well as contraction of smooth muscle. These $TxA_2$ mimics have also been used to develop inhibitors of $TxA_2$ action as they work through the activation of the thromboxane receptors called TP receptors.

Several thromboxane synthase inhibitors (TSI) have been reported, some based on imidazole (23). In general, the $IC_{50}$'s of the imidazole-based inhibitors were in the range $10^{-4}$-$10^{-7}$ m (24). Undesirable pressor effects that could not be resolved from their anti-thrombotic actions have been noted upon administration of these drugs, making the substituted imidazoles unsuitable for drug development.

Non-steroidal anti-inflammatory drugs such as aspirin have also been used to inhibit thromboxane synthesis. Aspirin, however, has frequent side effects, including gastric ulcers and Reye's syndrome. Attempts have been made to avoid these problems by developing COX-2 inhibitors such as CELEBREX® (Celecoxib) and VIOXX® (Rofecoxib) (42, 43). These drugs do not, however affect thromboxane formation in platelets where COX-1 is present and therefore are not of assitance in combatting thrombosis.

The hepoxilins are biologically active metabolites of arachidonic acid formed through the 12(S)-lipoxygenase pathway and hence are structurally unlike the prostaglandin endoperoxides (25-27). Four natural hepoxilins have been identified, the A-type hepoxilins consisting of two epimers having a hydroxyl group at carbon 8 (8(S, R)-hydroxy-11(S), 12(S)-epoxy-eicosa-5Z, 9E, 14Z-trienoic acid) and the B-type, two epimers having a hydroxyl group at carbon 10 (10(S,R)-hydroxy-11(S), 12(S)-epoxy-eicosa-5Z, 8Z,14Z-trienoic acid). Pharmacological studies have provided evidence that these compounds raise intracellular calcium by activating calcium stores in human neutrophils (28, 29). A hepoxilin-specific receptor responsible for this action has been suggested (30). The hepoxilins activate potassium channels in platelets (31) and in the Aplysia brain (32, 33). In platelets, the hepoxilins are formed endogenously in response of the cell to hypertonic volume expansion, and function to normalize cell volume (31).

Neither the hepoxilins nor the hepoxilin analogs described herein have previously been reported to affect thromboxane formation and action.

SUMMARY OF THE INVENTION

The present invention provides new methods and compositions for inhibiting thromboxane formation and antagonising thromboxane activity in mammals.

These methods can be used to treat thromboxane-mediated diseases including cardiovascular diseases, diabetes mellitus, hypertension, thrombosis and septic shock, or any disorder where it is desirable to reduce thromboxane formation and/or activity.

The invention further provides a method for treating eye diseases, associated with ocular inflammation and/or increased ocular pressure, by administration of hepoxilins or hepoxilin analogs as described herein.

In accordance with one embodiment, the present invention provides a method for inhibiting thromboxane formation in a mammal comprising administering to the mammal an effective amount of a hepoxilin or of a hepoxilin analog of the formula:

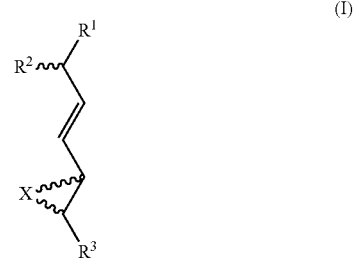

(I)

wherein X is O, $CH_2$, S or NH;

$R^1$ is lower alkyl or alkene;
lower alcohol (C1 to C22), saturated or unsaturated; or
—$CH_2CH$=$CH$— $(CH_2)_3$—$COR''$ wherein $R''$ is OH, O— lower alkyl or alkene;

$R^2$ is OH, $NH_2$, SH, $OPO_3H$, lower alkyl or alkene or O— lower alkyl or alkene; and $R^3$ is lower alkyl or alkene or
—$CH_2$—$CH$=$CH$—$(CH_2)_4$—$R'''$ wherein $R'''$ is $CH_3$, $CH_2OH$, $CH_2$—O— lower alkyl or alkene, phenyl or substituted phenyl

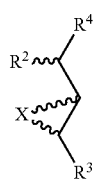

(II)

wherein X, $R^1$, $R^2$ and $R^3$ are as defined for formula I and $R^4$ is lower alkyl or alkene;

lower alcohol (C1 to C22), saturated or unsaturated; or

—CH═CH—CH$_2$—CH═CH—(CH$_2$)$_3$—COR"

wherein R"═OH or O— lower alkyl or alkene, or of a derivative thereof.

In accordance with a further embodiment, the present invention provides a method for inhibiting thromboxane formation in a mammal comprising administering to the mammal an effective amount of a compound selected from the group consisting of:
(a) 8(S)-hydroxy-11,12-cyclopropyl-eicosa-5Z,9E,14Z-trienoic acid or a derivative thereof;
(b) 8(R)-hydroxy-11,12-cyclopropyl-eicosa-5Z,9E,14Z-trienoic acid or a derivative thereof;
(c) 10(S)-hydroxy-11,12-cyclopropyl-eicosa-5Z,8Z,14Z-trienoic acid or a derivative-thereof; and
(d) 10(R)-hydroxy-11,12-cyclopropyl-eicosa-5Z,8Z,14Z-trienoic acid or a derivative thereof.

In accordance with a further embodiment, the present invention provides a method for antagonising thromboxane activity in a mammal comprising administering to the mammal an effective amount of a hepoxilin or of a hepoxilin analog of the formula:

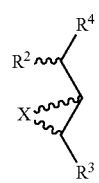

(II)

wherein X, $R^1$, $R^2$ and $R^3$ are as defined for formula I and $R^4$ is lower alkyl or alkene;

lower alcohol (C1 to C22), saturated or unsaturated; or

—CH═CH—CH$_2$—CH═CH—(CH$_2$)$_3$—COR"

wherein R"═OH or O— lower alkyl or alkene, or of a derivative thereof.

In accordance with a further embodiment, the present invention provides a method for antagonising thromboxane activity in a mammal comprising administering to the mammal an effective amount of a compound selected from the group consisting of:
(a) 8(S)-hydroxy-11,12-cyclopropyl-eicosa-5Z,9E,14Z-trienoic acid or a derivative thereof;
(b) 8(R)-hydroxy-11,12-cyclopropyl-eicosa-5Z,9E,14Z-trienoic acid or a derivative thereof;
(c) 10(S)-hydroxy-11,12-cyclopropyl-eicosa-5Z,8Z,14Z-trienoic acid or a derivative thereof; and
(d) 10(R)-hydroxy-11,12-cyclopropyl-eicosa-5Z,8Z,14Z-trienoic acid or a derivative thereof.

In accordance with a further embodiment, the present invention provides a method of preventing or reducing thromboxane-mediated platelet aggregation in a mammal comprising administering to the mammal an effective amount of a hepoxilin or of a hepoxilin analog of the formula:

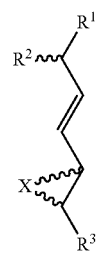

(I)

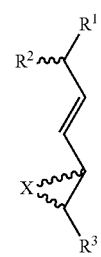

(I)

wherein X is O, CH$_2$, S or NH;

$R^1$ is lower alkyl or alkene;
  lower alcohol (C1 to C22), saturated or unsaturated; or
    —CH$_2$CH═CH—(CH$_2$)$_3$—COR" wherein R" is OH, O— lower alkyl or alkene;
$R^2$ is OH, NH$_2$, SH, OPO$_3$H, lower alkyl or alkene or O— lower alkyl or alkene; and
$R^3$ is lower alkyl or alkene or
    —CH$_2$—CH═CH—(CH$_2$)$_4$—R'" wherein R'" is CH$_3$, CH$_2$OH, CH$_2$—O— lower alkyl or alkene, phenyl or substituted phenyl or wherein X is O, CH$_2$, S or NH;

$R^1$ is lower alkyl or alkene;
  lower alcohol (C1 to C22), saturated or unsaturated; or
    —CH$_2$CH═CH—(CH$_2$)$_3$—COR" wherein R" is OH, O— lower alkyl or alkene;
$R^2$ is OH, NH$_2$, SH, OPO$_3$H, lower alkyl or alkene or O— lower alkyl or alkene; and
$R^3$ is lower alkyl or alkene or
    —CH$_2$—CH═CH—(CH$_2$)$_4$—R'" wherein R'" is CH$_3$, CH$_2$OH, CH$_2$—O— lower alkyl or alkene, phenyl or substituted phenyl

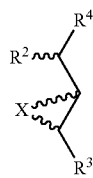

(II)

wherein X, $R^1$, $R^2$ and $R^3$ are as defined for formula I and $R^4$ is lower alkyl or alkene;

lower alcohol (C1 to C22), saturated or unsaturated; or

—CH=CH—$CH_2$—CH=CH—$(CH_2)_3$—COR"

wherein R"=OH or O— lower alkyl or alkene or a derivative thereof.

In accordance with a further embodiment, the present invention provides a method of preventing or reducing thromboxane-mediated platelet aggregation in a mammal comprising administering an effective amount of a compound selected from the group consisting of:

(a)  8(S)-hydroxy-11,12-cyclopropyl-eicosa-5Z,9E,14Z-trienoic acid or a derivative thereof;

(b)  8(R)-hydroxy-11,12-cyclopropyl-eicosa-5Z,9E,14Z-trienoic acid or a derivative thereof;

(c)  10(S)-hydroxy-11,12-cyclopropyl-eicosa-5Z,8Z,14Z-trienoic acid or a derivative thereof; and (d)  10(R)-hydroxy-11,12-cyclopropyl-eicosa-5Z,8Z,14Z-trienoic acid or a derivative thereof.

In accordance with a further embodiment, the present invention provides a method of treating a thromboxane-mediated disease in a mammal comprising administering to the mammal an effective amount of a hepoxilin or of a hepoxilin analog of the formula:

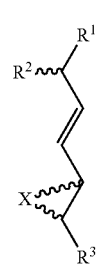

(I)

wherein X is O, $CH_2$, S or NH;

$R^1$ is lower alkyl or alkene;

lower alcohol (C1 to C22), saturated or unsaturated; or

—$CH_2$CH=CH—$(CH_2)_3$—COR" wherein R" is OH, O— lower alkyl or alkene;

$R^2$ is OH, $NH_2$, SH, $OPO_3H$, lower alkyl or alkene or O— lower alkyl or alkene; and $R^3$ is lower alkyl or alkene or —$CH_2$—CH=CH—$(CH_2)_4$—R'" wherein R'" is $CH_3$, $CH_2OH$, $CH_2$—O— lower alkyl or alkene, phenyl or substituted phenyl or

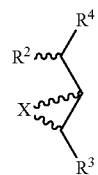

(II)

wherein X, $R^1$, $R^2$ and $R^3$ are as defined for formula I and $R^4$ is lower alkyl or alkene;

lower alcohol (C1 to C22), saturated or unsaturated; or

—CH=CH—$CH_2$—CH=CH—$(CH_2)_3$—COR"

wherein R"=OH or O— lower alkyl or alkene or a derivative thereof.

In accordance with a further embodiment, the present invention provides a method of treating a thromboxane-mediated disease in a mammal comprising administering to the mammal an effective amount of a compound selected from the group consisting of:

(a)  8(S)-hydroxy-11,12-cyclopropyl-eicosa-5Z,9E,14Z-trienoic acid or a derivative thereof;

(b)  8(R)-hydroxy-11,12-cyclopropyl-eicosa-5Z,9E,14Z-trienoic acid or a derivative thereof;

(c)  10(S)-hydroxy-11,12-cyclopropyl-eicosa-5Z,8Z,14Z-trienoic acid or a derivative thereof; and (d)  10(R)-hydroxy-11,12-cyclopropyl-eicosa-5Z,8Z,14Z-trienoic acid or a derivative thereof.

In accordance with a further embodiment, the present invention provides a method for treating or preventing an eye disease associated with ocular inflammation and/or increased intraocular pressure comprising administering to the mammal an effective amount of a hepoxilin or of a hepoxilin analog of the formula:

(I)

wherein X is O, $CH_2$, S or NH;

$R^1$ is lower alkyl or alkene;

lower alcohol (C1 to C22), saturated or unsaturated; or

—$CH_2$CH=CH—$(CH_2)_3$—COR" wherein R" is OH, O— lower alkyl or alkene;

$R^2$ is OH, $NH_2$, SH, $OPO_3H$, lower alkyl or alkene or O— lower alkyl or alkene; and $R^3$ is lower alkyl or alkene or —$CH_2$—CH=CH—$(CH_2)_4$—R'" wherein R'" is $CH_3$, $CH_2OH$, $CH_2$—O— lower alkyl or alkene, phenyl or substituted phenyl or

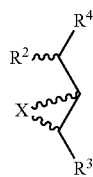

(II)

wherein X, $R^1$, $R^2$ and $R^3$ are as defined for formula I and $R^4$ is lower alkyl or alkene;

lower alcohol (C1 to C22), saturated or unsaturated; or

—CH═CH—CH$_2$—CH═CH—(CH$_2$)$_3$—COR"

wherein R"═OH or O— lower alkyl or alkene or a derivative thereof.

In accordance with a further embodiment, the present invention provides a method for treating or preventing an eye disease associated with ocular inflammation and/or increased intraocular pressure comprising administering to the mammal an effective amount of a compound selected from the group consisting of:

(a)     8(S)-hydroxy-11,12-cyclopropyl-eicosa-5Z,9E,14Z-trienoic acid or a derivative thereof;

(b)     8(R)-hydroxy-11,12-cyclopropyl-eicosa-5Z,9E,14Z-trienoic acid or a derivative thereof;

(c)     10(S)-hydroxy-11,12-cyclopropyl-eicosa-5Z,8Z,14Z-trienoic acid or a derivative thereof; and (d)     10(R)-hydroxy-11,12-cyclopropyl-eicosa-5Z,8Z,14Z-trienoic acid or a derivative thereof.

In accordance with a further embodiment, the present invention provides a method for reducing intra-ocular pressure in a mammal comprising administering intra-ocularly to the mammal an effective amount of at least one of a hepoxilin or of a hepoxilin analog of the formula:

(I)

wherein X is O, CH$_2$, S or NH;

$R^1$ is lower alkyl or alkene;

lower alcohol (C1 to C22), saturated or unsaturated; or

—CH$_2$CH═CH—(CH$_2$)$_3$—COR" wherein R" is OH, O— lower alkyl or alkene;

$R^2$ is OH, NH$_2$, SH, OPO$_3$H, lower alkyl or alkene or O— lower alkyl or alkene; and $R^3$ is lower alkyl or alkene or —CH$_2$—CH═CH—(CH$_2$)$_4$—R'" wherein R'" is CH$_3$, CH$_2$OH, CH$_2$—O— lower alkyl or alkene, phenyl or substituted phenyl or

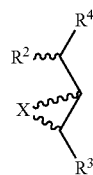

(II)

wherein X, $R^1$, $R^2$ and $R^3$ are as defined for formula I and $R^4$ is lower alkyl or alkene;

lower alcohol (C1 to C22), saturated or unsaturated; or

—CH═CH—CH$_2$—CH═CH—(CH$_2$)$_3$—COR"

wherein R"═OH or O— lower alkyl or alkene or a derivative thereof.

In accordance with a further embodiment, the present invention provides a method for reducing intra-ocular pressure in a mammal comprising administering intra-ocularly to the mammal an effective amount of a compound selected from the group consisting of:

(a)     8(S)-hydroxy-11,12-cyclopropyl-eicosa-5Z,9E,14Z-trienoic acid or a derivative thereof;

(b)     8(R)-hydroxy-11,12-cyclopropyl-eicosa-5Z,9E,14Z-trienoic acid or a derivative thereof;

(c)     10(S)-hydroxy-11,12-cyclopropyl-eicosa-5Z,8Z,14Z-trienoic acid or a derivative thereof; and (d)     10(R)-hydroxy-11,12-cyclopropyl-eicosa-5Z,8Z,14Z-trienoic acid or a derivative thereof.

In accordance with a further embodiment, the present invention provides use of a compound of the formula:

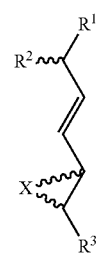

(I)

wherein X is O, CH$_2$, S or NH;

$R^1$ is lower alkyl or alkene;

lower alcohol (C1 to C22), saturated or unsaturated; or

—CH$_2$CH═CH—(CH$_2$)$_3$—COR" wherein R" is OH, O— lower alkyl or alkene;

$R^2$ is OH, NH$_2$, SH, OPO$_3$H, lower alkyl or alkene or O— lower alkyl or alkene; and $R^3$ is lower alkyl or alkene or —CH$_2$—CH═CH—(CH$_2$)$_4$—R'" wherein R'" is CH$_3$, CH$_2$OH, CH$_2$—O— lower alkyl or alkene, phenyl or substituted phenyl wherein X is O, $CH_2$, S or NH;
$R^1$ is lower alkyl or alkene;
lower alcohol (C1 to C22), saturated or unsaturated; or
—$CH_2CH$=$CH$—$(CH_2)_3$—$COR''$ wherein $R''$ is OH, O— lower alkyl or alkene;
$R^2$ is OH, $NH_2$, SH, $OPO_3H$, lower alkyl or alkene or O— lower alkyl or alkene; and
$R^3$ is lower alkyl or alkene or
—$CH_2$—$CH$=$CH$—$(CH_2)_4$—$R'''$ wherein $R'''$ is $CH_3$, $CH_2OH$, $CH_2$—O— lower alkyl or alkene, phenyl or substituted phenyl or

(II)

wherein X, $R^1$, $R^2$ and $R^3$ are as defined for formula I and $R^4$ is lower alkyl or alkene;
lower alcohol (C1 to C22), saturated or unsaturated; or
—$CH$=$CH$—$CH_2$—$CH$=$CH$—$(CH_2)_3$—$COR''$
wherein $R''$=OH or O— lower alkyl or alkene, or a derivative thereof.

In accordance with a further embodiment, the present invention provides a composition for application to the eye comprising as active ingredient a compound selected from the group consisting of:
(a) 8(S)-hydroxy-11,12-cyclopropyl-eicosa-5Z,9E,14Z-trienoic acid or a derivative thereof;
(b) 8(R)-hydroxy-11,12-cyclopropyl-eicosa-5Z,9E,14Z-trienoic acid or a derivative thereof;
(c) 10(S)-hydroxy-11,12-cyclopropyl-eicosa-5Z,8Z,14Z-trienoic acid or a derivative thereof; and
(d) 10(R)hydroxy-11,12-cyclopropyl-eicosa-5Z,8Z,14Z-trienoic acid or a derivative thereof.

SUMMARY OF THE DRAWINGS

Certain embodiments of the invention are described, reference being made to the accompanying drawings, wherein:
FIG. 2 shows dose response curves for the anti-aggregatory effects of the four PBT compounds shown in FIG. 1. For or

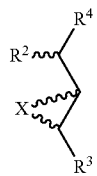

(II)

wherein X, $R^1$, $R^2$ and $R^3$ are as defined for formula I and $R^4$ is lower alkyl or alkene;
lower alcohol (C1 to C22), saturated or unsaturated; or
—$CH$=$CH$—$CH_2$—$CH$=$CH$—$(CH_2)_3$—$COR''$
wherein $R''$=OH or O— lower alkyl or alkene, or a derivative thereof, for the preparation of a medicament for a treatment selected from the group consisting of:

(a) for inhibiting thromboxane formation in a mammal;
(b) for treating or preventing eye disease associated with ocular inflammation and/or increased intraocular pressure in a mammal;
(c) for inhibiting thromboxane activity in a mammal;
(d) for preventing or reducing thromboxane-mediated platelet aggregation in a mammal;
(e) for treating a thromboxane-mediated disease in a mammal; and
(f) for reducing intra-ocular pressure in a mammal.

In accordance with a further embodiment, the present invention provides use of a compound selected from the group consisting of:

(a) 8(S)-hydroxy-11,12-cyclopropyl-eicosa-5Z,9E,14Z-trienoic acid or a derivative thereof;
(b) 8(R)-hydroxy-11,12-cyclopropyl-eicosa-5Z,9E,14Z-trienoic acid or a derivative thereof;
(c) 10(S)-hydroxy-11,12-cyclopropyl-eicosa-5Z,8Z,14Z-trienoic acid or a derivative thereof; and
(d) 10(R)-hydroxy-11,12-cyclopropyl-eicosa-5Z,8Z,14Z-trienoic acid or a derivative thereof,
for a treatment selected from the group consisting of:

(a) for inhibiting thromboxane formation in a mammal;
(b) for treating or preventing eye disease associated with ocular inflammation and/or increased intraocular pressure in a mammal;
(c) for inhibiting thromboxane activity in a mammal;
(d) for preventing or reducing thromboxane-mediated platelet aggregation in a mammal;
(e) for treating a thromboxane-mediated disease in a mammal; and
(f) for reducing intra-ocular pressure in a mammal.

In accordance with a further embodiment, the present invention provides a composition for application to the eye comprising as active ingredient a compound of the formula:

comparison, the effects of the four native hepoxilins are shown. The corresponding IC50 for each compound is shown.

Figure 1:
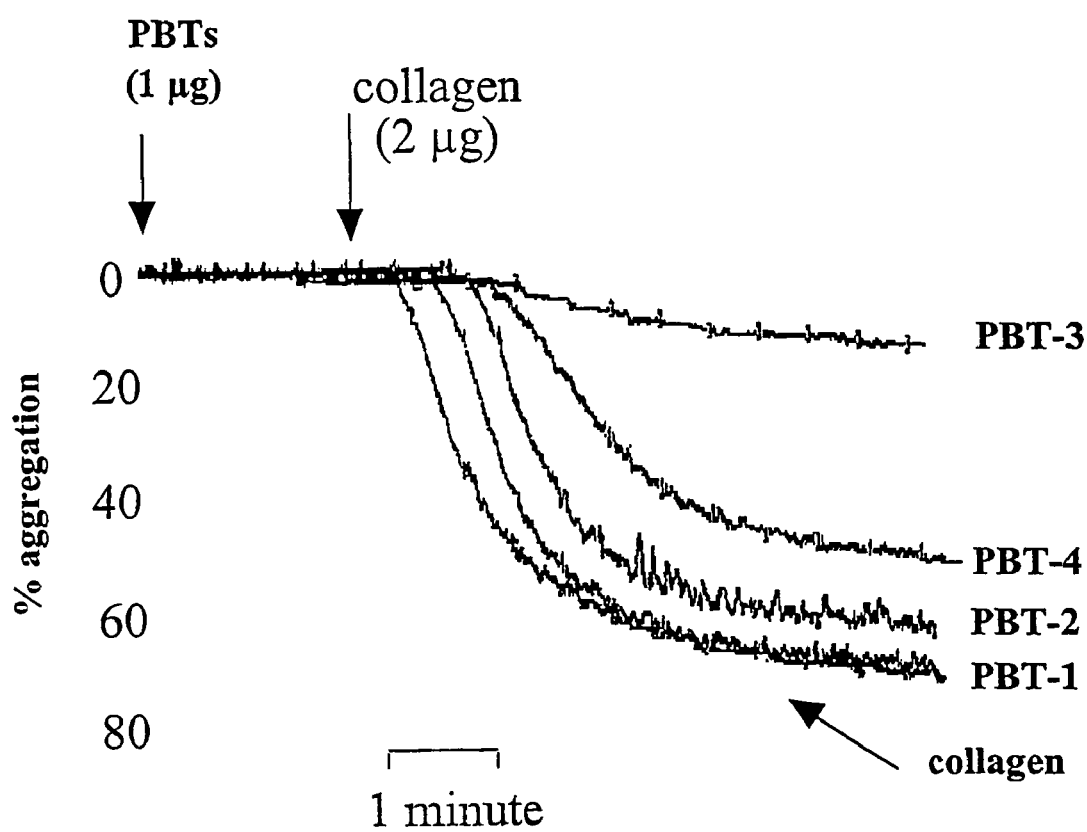
FIG. 1 shows inhibitory effects of four hepoxilin analogs, PBT-1 to PBT-4 on the collagen-evoked aggregation of human platelets. Typical inhibitory curves are shown. The PBT compounds (1 µg each) were added to washed platelets in a cuvette 2 min prior to the addition of collagen (2 µg) to the cuvette containing 350×106 platelets in 0.5 ml volume.
Figure 2:
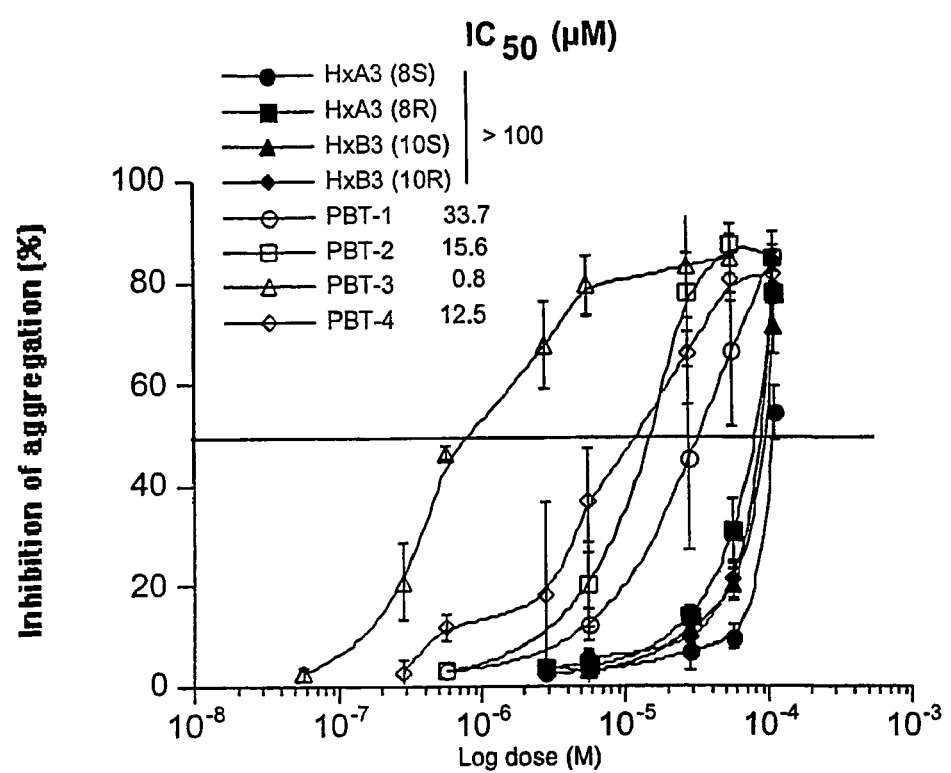
Figure 3:
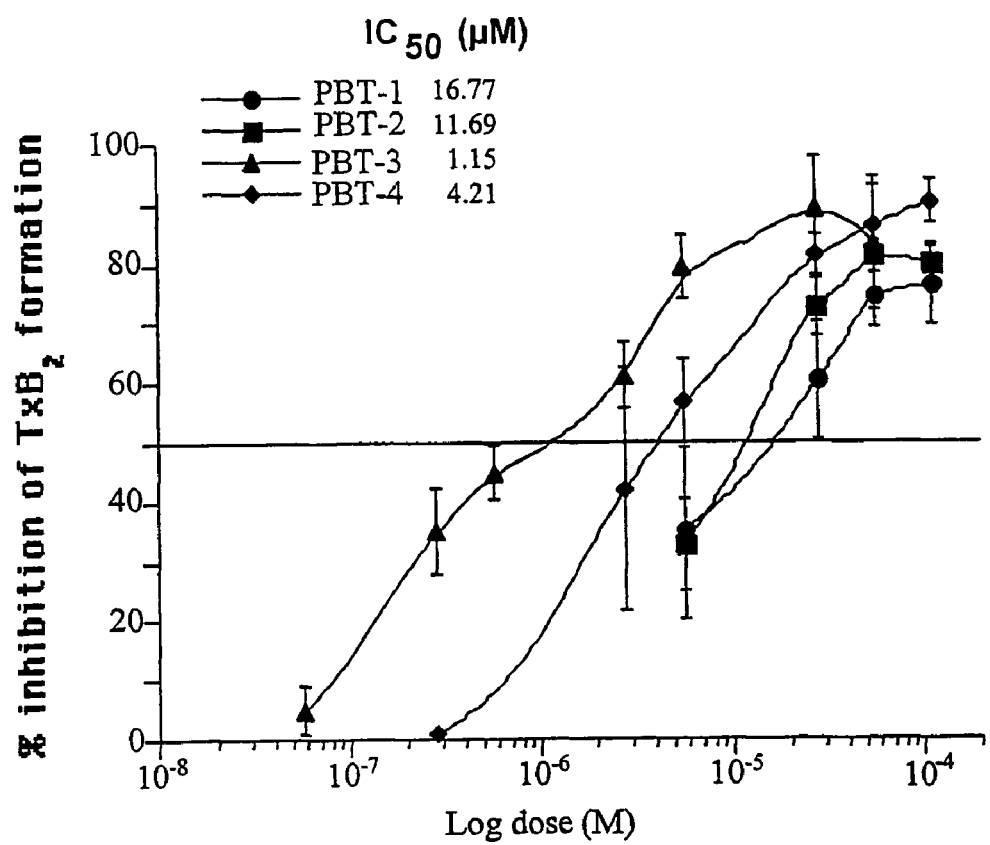

FIG. 3 shows dose response curves for the inhibitory effect of the four PBT compounds on TxB2 formation evoked by collagen. Experimental details are as shown in FIG. 1. The contents of the cuvettes, after aggregation was complete (5 min), were extracted with ethyl acetate as described in the Methods section, and the extracted compounds were converted into the ADAM-acetate fluorescent derivatives and TxB2 was quantified by HPLC. The IC50 for TxB2 inhibition compares favourably with that for inhibition of aggregation shown in FIG. 2.

Figure 4:
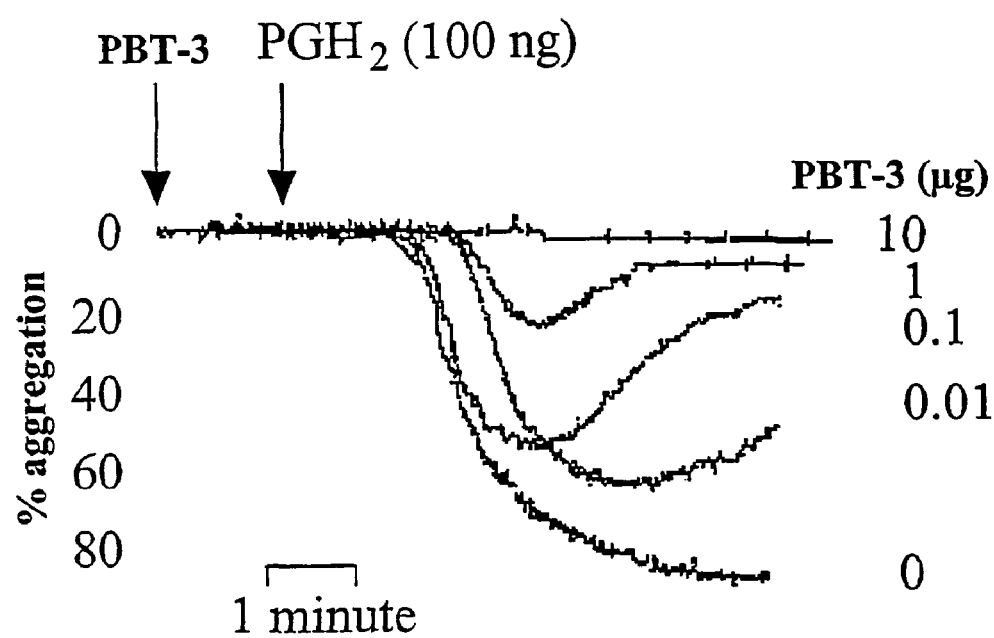

FIG. 4 shows inhibition of PGH2-evoked platelet aggregation by PBT-3. PGH2 was used at 100 ng, and the amounts of PBT-3 are shown for each inhibitory curve.

Figure 5:
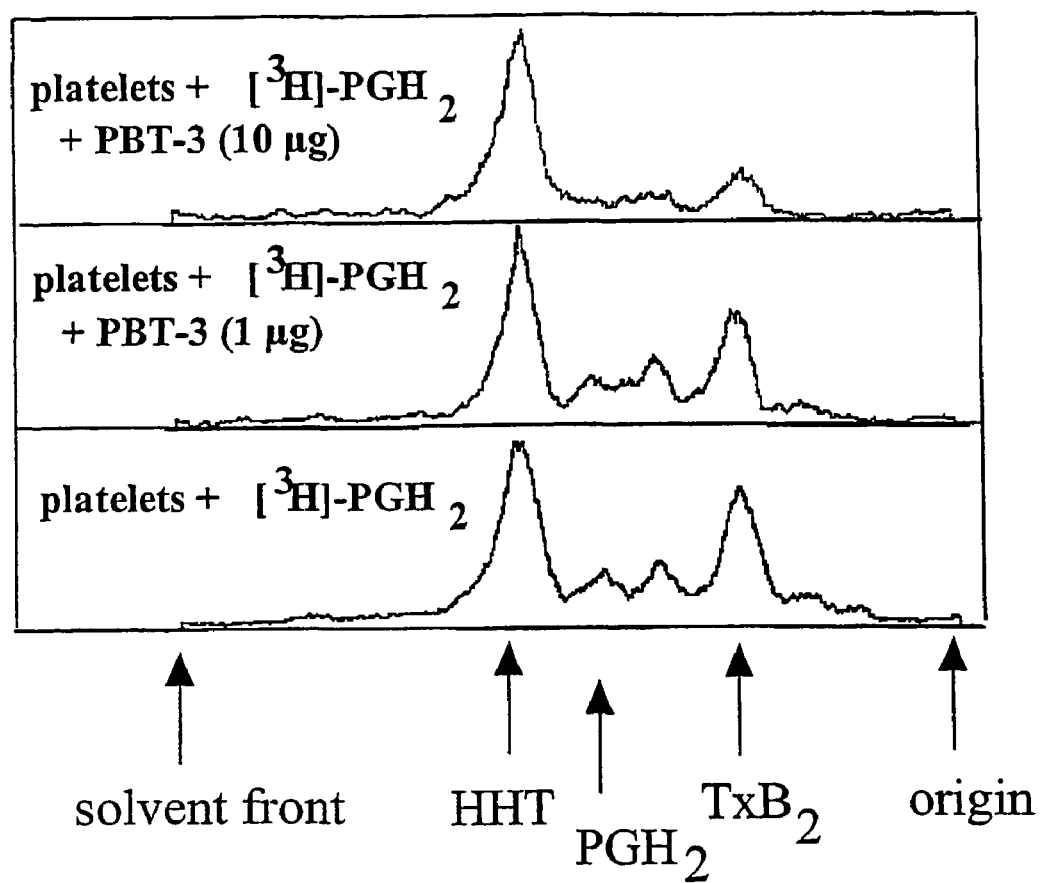

FIG. 5 shows metabolism of [3H]-PGH2 by human platelets and inhibition of formation of tritiated TxB2 by PBT-3. Tritiated PGH2 was admixed with unlabeled PGH2 and added to platelet suspensions in a cuvette 2 min after the addition of PBT-3. Aggregation (or its inhibition) was followed as shown in FIG. 4. The reaction was stopped at two minutes after addition of PGH2 and the contents of the cuvette were extracted with ethyl acetate. The distribution of radioactivity among various products was assessed by TLC.

Figure 6:
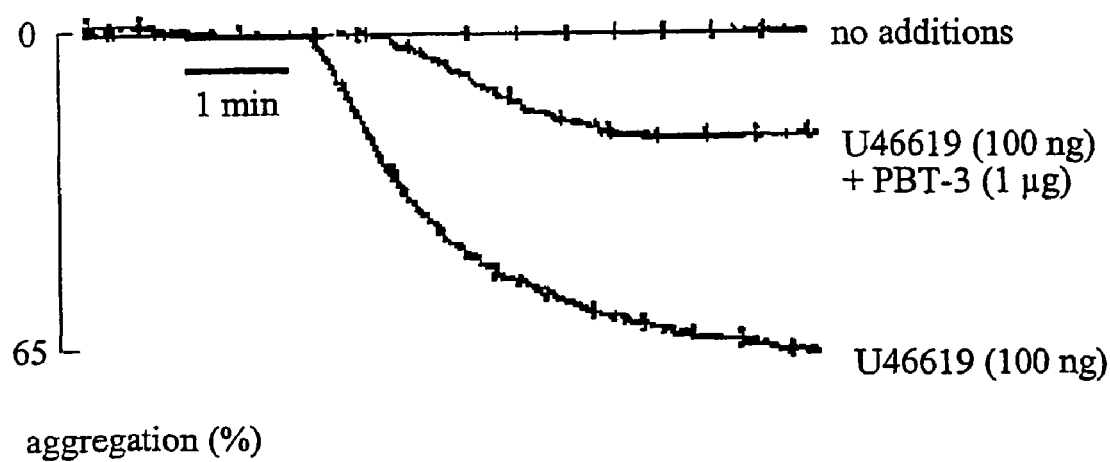

FIG. 6 shows the inhibitory effect of PBT-3 on platelet aggregation evoked by the $TxA_2$ mimic, U46619.

Figure 7A:
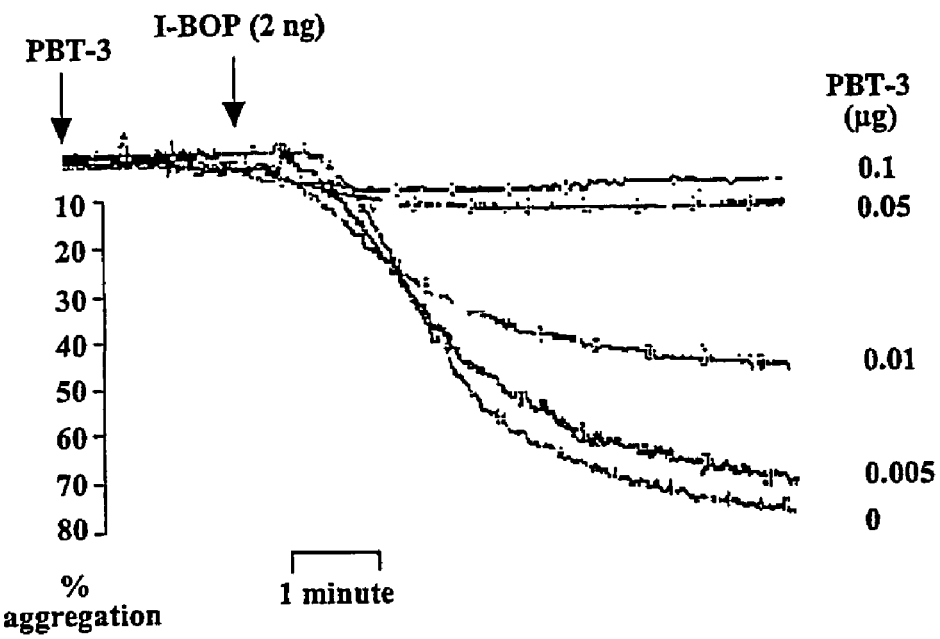

FIG. 7A shows the effect of various doses of the hepoxilin analog PBT-3 on platelet aggregation evoked by I-BOP. Values shown are typical of three separate experiments.

Figure 7B:
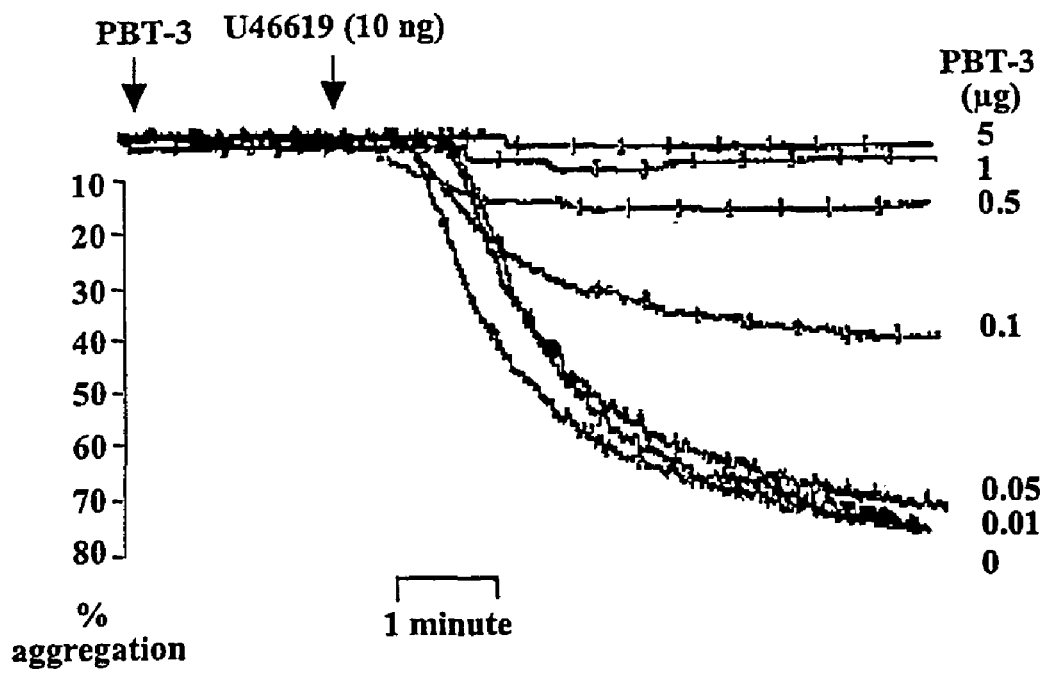

FIG. 7B shows the effect of various doses of the hepoxilin analog PBT-3 on platelet aggregation evoked by the thromboxane analog U46619.

Figure 8:
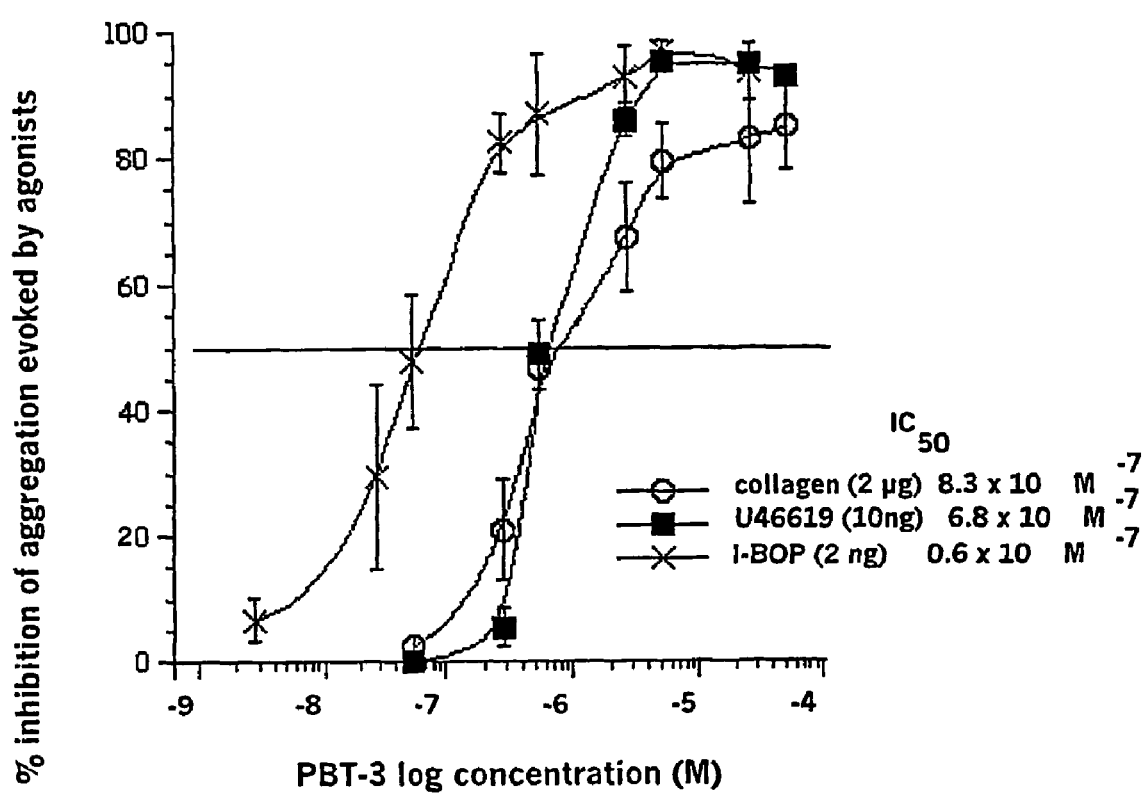

FIG. 8 shows dose response curves for the inhibition by PBT-3 of platelet aggregation evoked by collagen, U46619 and I-BOP. Values represent data from three separate experiments ±SD.

Figure 9:
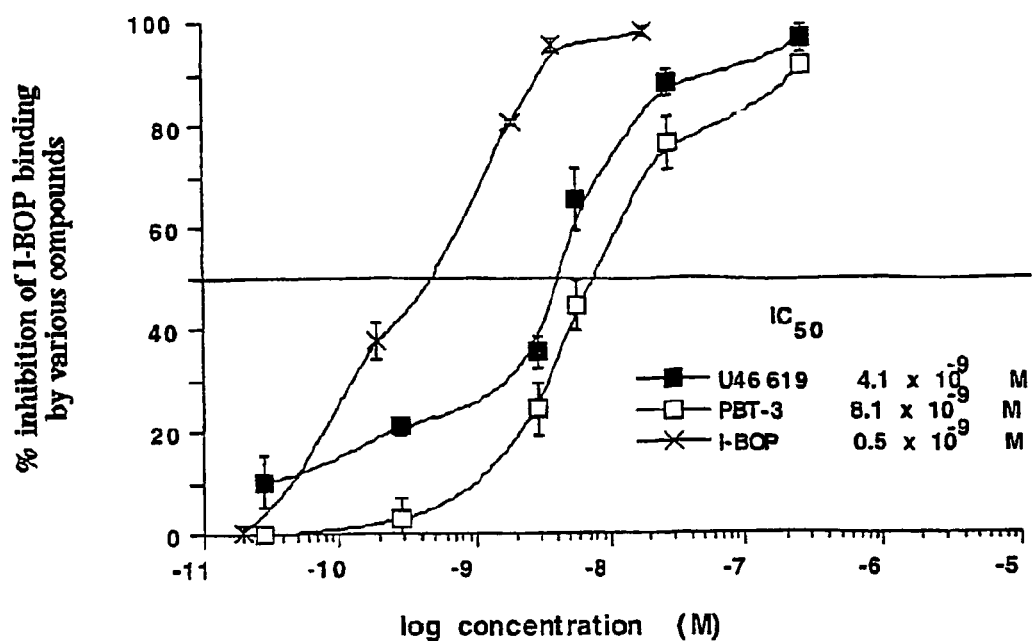

FIG. 9 shows dose response curves for the inhibition of binding of $^{125}$I-BOP binding to platelets by U46619, PBT-3 and I-BOP.

Figure 10:
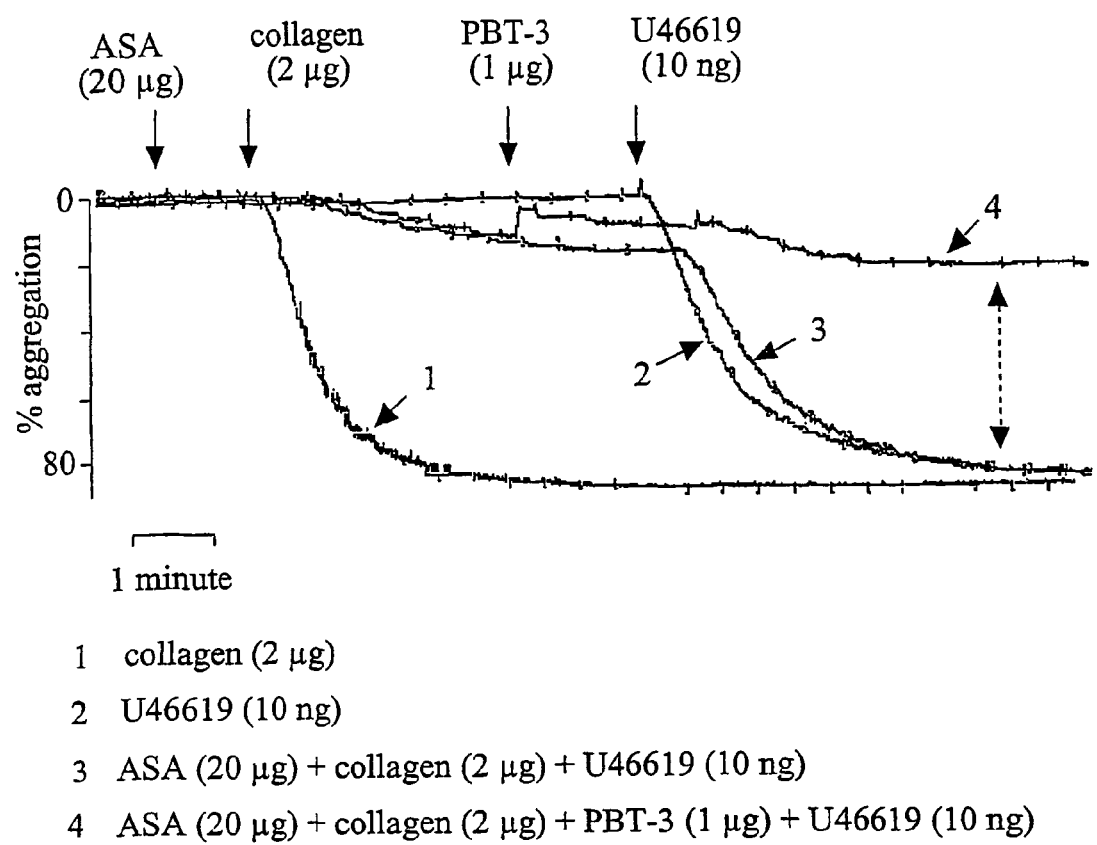

FIG. 10 shows the inhibitory effect of PBT-3 on platelet aggregation evoked by collagen or U46619 in the presence of ASA. Arrows indicate the time of addition of the various substances identified by number.

Figure 11:
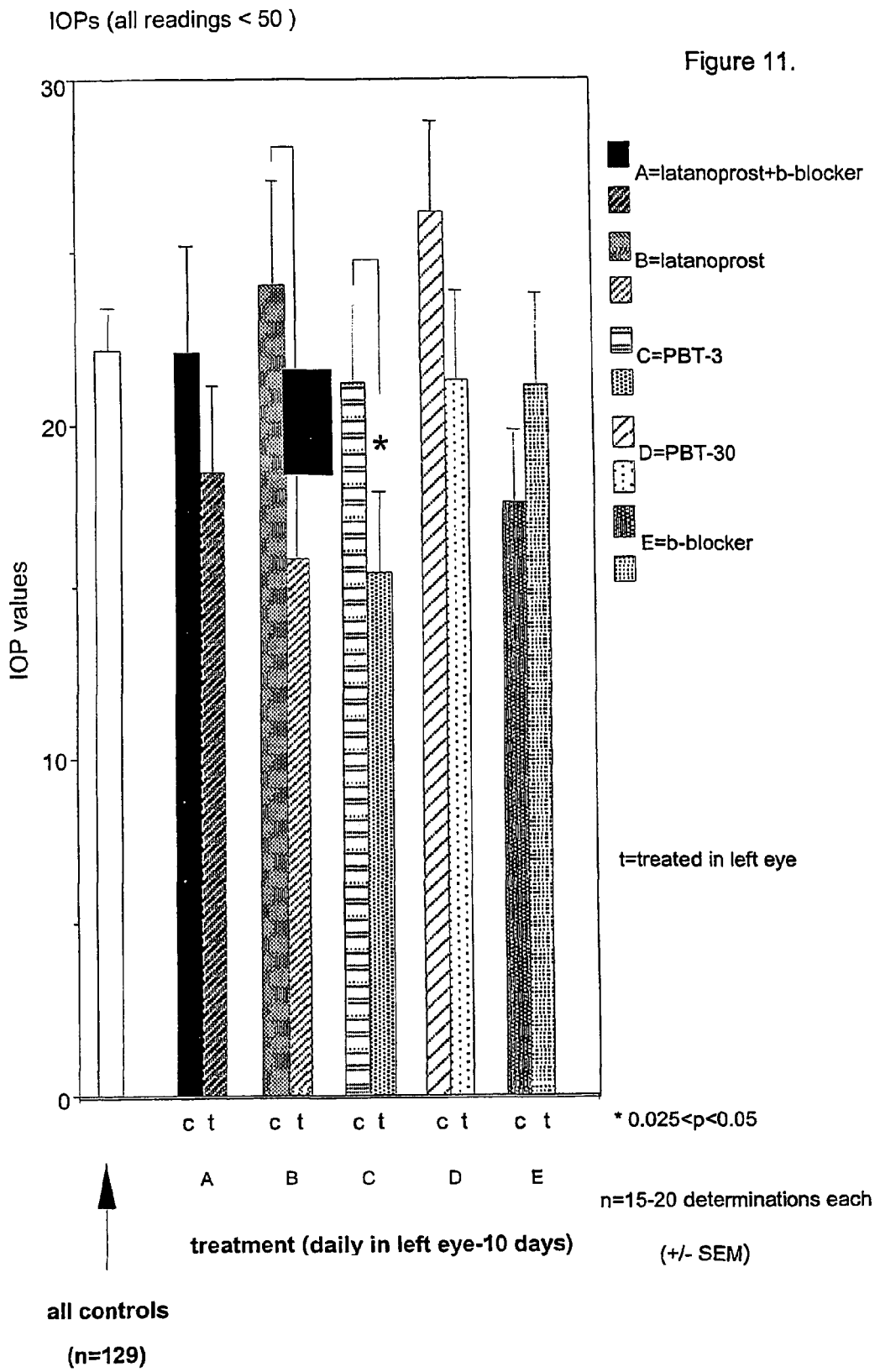

FIG. 11 shows intra-ocular pressure (IOP) in treated (t) and control (c) eyes of rats; treatments were A: 0.005% latanoprost+0.5% o-bunolol; B: 0.005% latanoprost; C: 0.005% PBT-3; D: 0.005% PBT-30; and E: 0.05% o-bunolol. Open bar on far left is mean IOP of all control (untreated) eyes (n=129).

Figure 12:
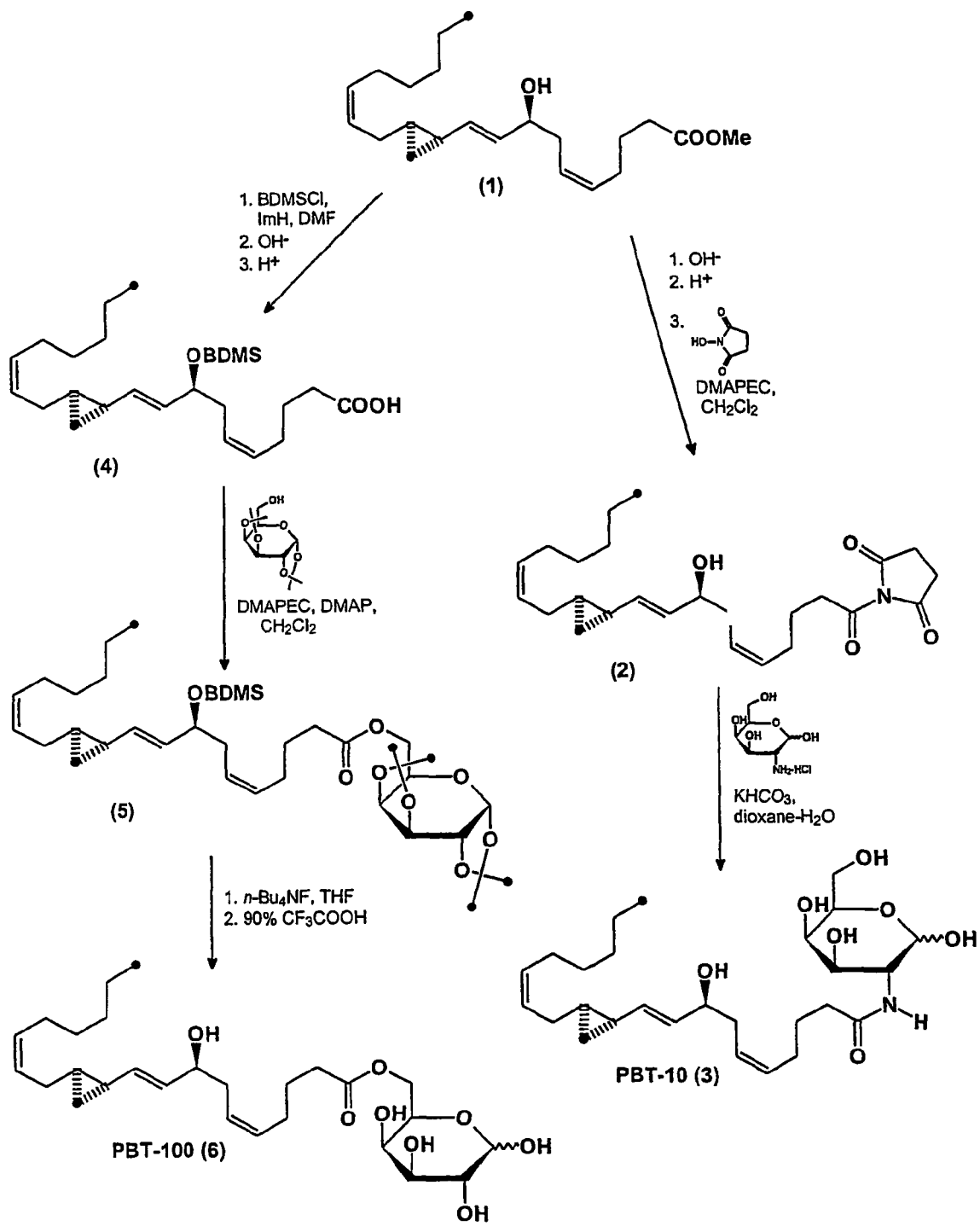

FIG. 12 is a schematic diagram of the chemical synthesis of galactose amide derivatives of hepoxilin analogs.

Figure 13:
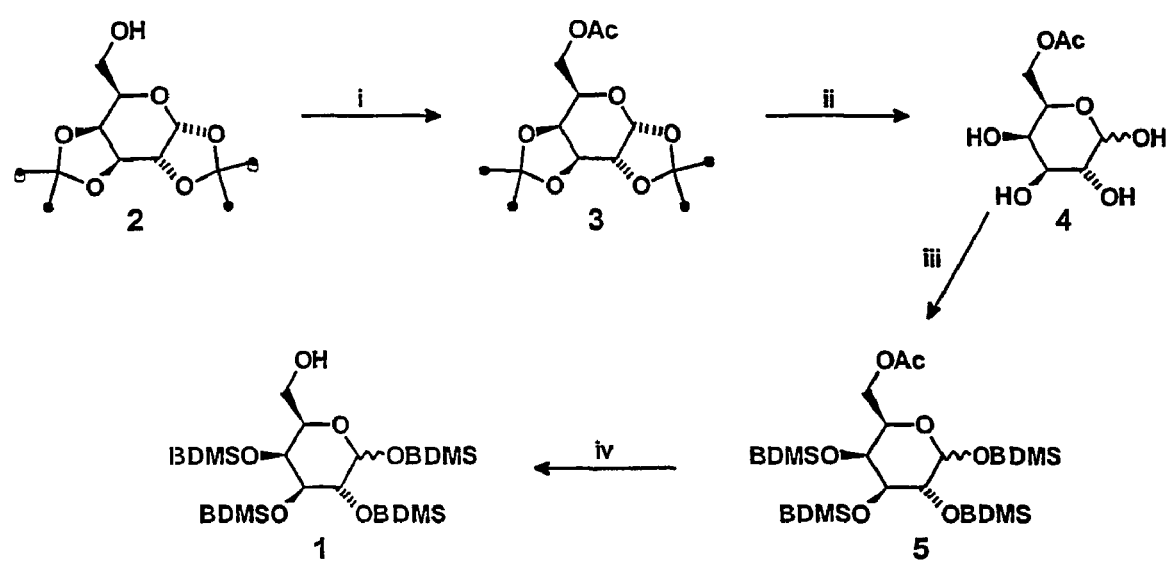

FIG. 13 is a schematic diagram of the chemical synthesis of a protected galactose intermediate. Reagents and conditions: i, $Ac_2O$, Py; ii, 90% TFA/$H_2O$; iii, BDMSCl, ImH, DMF; iv, 1N NaOH, MeOH—$H_2O$.

Figure 14:
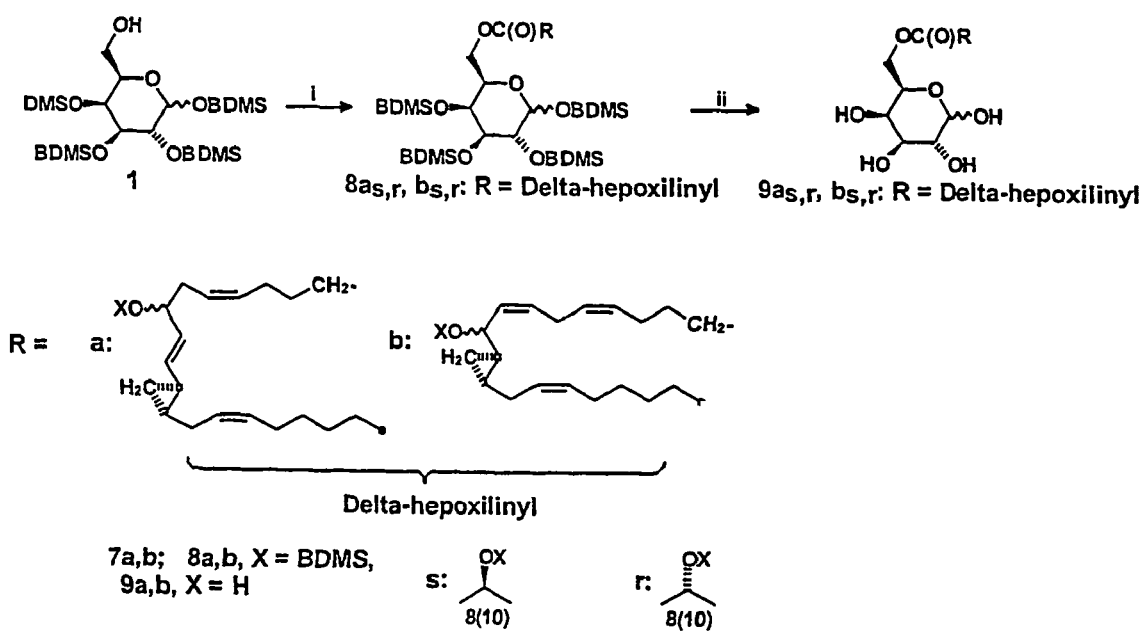

FIG. 14 is a schematic diagram of the chemical synthesis of hepoxilin galactose esters. Reagents and conditions: i, RCOOH (7a,b), EDAC, DMAP, $CH_2Cl_2$; ii, n-$Bu_4$NF, Py.HCl, THF

DETAILED DESCRIPTION OF THE INVENTION

In accordance with one embodiment, the present invention provides methods and pharmaceutical compositions for inhibiting thromboxane formation in a mammal.

These methods and compositions employ as active ingredient a natural hepoxilin or a hepoxilin analog.

As used herein, a "hepoxilin" means a naturally occurring hepoxilin. Naturally occurring hepoxilins include A-type hepoxilins consisting of two epimers having a hydroxyl group at carbon 8 (8(S, R)-hydroxy-11(S), 12(S)-epoxy-eicosa-5Z, 9E, 14Z-trienoic acid) and B-type, consisting of two epimers having a hydroxyl group at carbon 10 (10(S,R)-hydroxy-11(S), 12(S)-epoxy-eicosa-5Z, 8Z,14Z-trienoic acid).

In the hepoxilin analogs employed in the methods and compositions of the invention, the epoxide at C11-C12 of the native hepoxilins is replaced by another group, such as S, —NH or —$C_nH_{2n}$, where n is 1 to 4.

Hepoxilin analogs which may be used in the methods of the invention comprise compounds of the formula

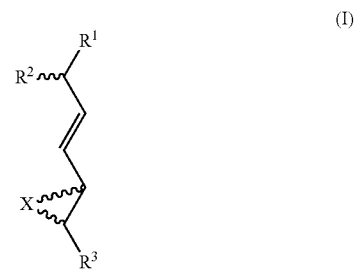

(I)

wherein X=O, $CH_2$, S or NH;
R$^1$=lower alkyl or alkene;
  lower alcohol (C1 to C22), saturated or unsaturated; or
  —$CH_2CH$=CH—$(CH_2)_3$—COR″ wherein R″=OH or
  O— lower alkyl or alkene;
R$^2$=OH, $NH_2$, SH, $OPO_3H$, lower alkyl or alkene or O—
  lower alkyl or alkene; and
R$^3$=lower alkyl or alkene or
  —$CH_2$—CH=CH—$(CH_2)_4$—R‴ wherein R‴=$CH_3$,
  $CH_2OH$ or $CH_2$—O— lower alkyl or alkene or phenyl
  and substituted phenyl
  or

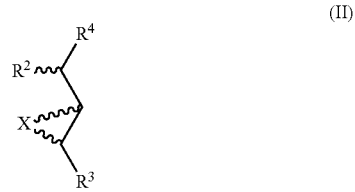

(II)

wherein X, R$^1$, R$^2$ and R$^3$ are as in formula I and R$^4$ lower alkyl or alkene;
lower alcohol (C1 to C22), saturated or unsaturated; or
—CH=CH—$CH_2$—CH=CH—$(CH_2)_3$—COR″
wherein R″=OH or O— lower alkyl or alkene, and
derivatives of these compounds, including water soluble derivatives of these compounds, such as sugar amides and sugar esters of the compounds.

As used herein, "alkyl" means a branched or unbranched alkyl radical. "Lower alkyl or alkene" means C1 to C22 alkyl or alkene.

Substituted phenyl includes phenyl substituted with —OH, I, Br, Cl or lower alkyl or alkene.

Preferred hepoxilin analogs are:

PBT-1 which is 8(S)-hydroxy-11,12-cyclopropyl-eicosa-5Z,9E,14Z-trienoic acid methyl ester, or the corresponding free acid;

PBT-2 which is 8(R)-hydroxy-11,12-cyclopropyl-eicosa-5Z,9E,14Z-trienoic acid methyl ester, or the corresponding free acid;

PBT-3 which is 10(S)-hydroxy-11,12-cyclopropyl-eicosa-5Z,8Z,14Z-trienoic acid methyl ester, or the corresponding free acid; and PBT-4 which is 10(R)-hydroxy-11,12-cyclopropyl-eicosa-5Z,8Z,14Z-trienoic acid methyl ester, or the corresponding free acid. These analogs are described in U.S. Pat. No. 5,616,607, the contents of which are incorporated herein by reference. Further preferred analogs are the sugar amide and sugar ester derivatives of these analogs, including the galactose amides and esters thereof.

Water-soluble derivatives of the hepoxilins and hepoxilin analogs described herein include sugar amides and sugar esters of the analogs; suitable sugars include monosaccharides such as galactose, glucose and fructose.

The ability to inhibit thromboxane formation in a mammal using hepoxilins and hepoxilin analogs described herein enables methods and pharmaceutical compositions useful in the treatment of disorders associated with an increased or undesirable level of thromboxane or of thromboxane formation or action, or disorders associated with an undesirable balance between thromboxane and another compound, such as a prostaglandin.

Such disorders include cardiovascular disease, diabetes mellitus, hypertension, thrombosis and septic shock.

The specific regulation of arachidonic acid metabolism at various steps in its enzymatic metabolism into different products is of significant interest. Total blockade of the whole prostaglandin pathway is not always desirable. For example, cyclooxygenase inhibitors block the whole prostaglandin pathway, eliminating the formation not only of prostaglandins and thromboxane but also of prostacyclin, a powerful anti-thrombotic agent. In certain diseases, such as diabetes mellitus, where the ratio of thromboxane to prostacyclin favours thromboxane, diabetic vascular complications can result from such excessive thromboxane formation. What is required in such thromboxane-mediated conditions is inhibition only of thromboxane formation and not of prostacyclin or prostaglandin $E_2$. In fact, enhancing prostacyclin formation could benefit in the control of these vascular complications.

The present invention provides methods and pharmaceutical compositions which inhibit thromboxane formation and therefore serve to restore a more normal thromboxane/prostaglandin balance. This inhibition is due, at least in part, to inhibition of thromboxane synthase by hepoxilins and hepoxilin analogs as described herein.

In accordance with a further embodiment, hepoxilins and hepoxilin analogs inhibit platelet aggregation evoked by thromboxane or by a thromboxane analog.

Collagen activates the release from platelets of arachidonic acid, which is then converted into products via two competing pathways, one through cyclooxygenase to form the prostaglandin endoperoxide intermediate $PGH_2$, followed in turn by its conversion into the pro-thrombotic unstable compound, thromboxane $A_2$ ($TxA_2$ (detected as $TxB_2$), and the other through 12(S)-lipoxygenase to form the intermediate 12(S)-HPETE, which in turn is converted into 12(S)-HETE and the native hepoxilins.

It is clear from the data shown herein that the inhibition of thromboxane-evoked platelet aggregation by hepoxilins and hepoxilin analogs involves both inhibition of thromboxane formation and antagonism of thromboxane activity mediated through TP receptors, the latter effect being seen at lower hepoxilin analog concentrations than the inhibition of thromboxane formation.

In a further embodiment, the invention provides methods and compositions for antagonising thromboxane action, employing the hepoxilins and hepoxilin analogs described herein. The hepoxilin analog PBT-3, for example, shows an affinity for TP receptors similar to that of the thromboxane agonist U46619, indicating its potential as a potent thromboxane antagonist.

The hepoxilin analogs described herein have been shown to be non-toxic and well tolerated in in vitro animal studies at concentrations up to 40 mg/kg (46).

The invention further enables methods and compositions for treating eye diseases involving ocular inflammation and/or increased intra ocular pressure, including glaucoma and diabetic neuropathy. As disclosed herein, hepoxilin analogs have been shown to reduce intra ocular pressure when administered directly to the eye in the form of eye drops; the hepoxilin analogs were as effective as the current drug of choice for lowering intra ocular pressure, latanoprost. The hepoxilin analogs also are able to reduce tissue inflammation. Hepoxilins and hepoxilin analogs provide a new family of drugs for the treatment of eye diseases, with the ability both to reduce inflammation and to reduce intra ocular pressure, with the potential to protect against or reverse optic nerve damage in diseases such as glaucoma and diabetic neuropathy.

The mechanism of the observed effect of hepoxilins and hepoxilin analogs on intra ocular eye pressure is presently uncertain but a clear pressure-lowering effect was demonstrated.

In accordance with the methods and compositions of the present invention, one or more hepoxilins or hepoxilin analogs may be administered to a mammal in a variety of forms depending on the selected route of administration, as will be understood by those skilled in the art. The compositions of the invention may be administered orally or parentally, the latter route including intravenous and subcutaneous administration. Parenteral administration may be by continuous infusion over a selected period of time. Forms for injectable use include sterile aqueous solutions or dispersion and sterile powders for the extemporaneous preparation of sterile injectable solutions or dispersions. In all cases the form must be sterile and must be fluid to the extent that easy syringability exists.

In a further embodiment, one or more hepoxilins or hepoxilin analogs may be administered intra ocularly. Compositions for intra ocular use include eye drops comprising the hepoxilin or hepoxilin analog dissolved in a fluid acceptable for intra ocular administration. A physiological saline may, for example, be used.

The hepoxilin or hepoxilin analog may be orally administered with an inert diluent or with an assimilable edible carrier, or it may be enclosed in hard or soft shell gelatin capsules, compressed into tablets or incorporated directly with the food of the diet. For oral therapeutic administration, a hepoxilin analog may be incorporated with excipient and used in the form in ingestible tablets, buccal tablets, troches, capsules, elixirs, suspensions syrups, wafers and the like.

Compositions containing one or more hepoxilins or hepoxilin analogs of the present invention can also be administered in a solution or emulsion contained within phospholipid vesicles called liposomes. The liposomes may be unilamellar or multilamellar and are formed of constituents selected from phosphatidylcholine, dipalmitoylphosphatidylcholine, cholesterol, phosphatidylethanolamtine, phosphatidylserine, dimyristoylphosphatidylcholine and combinations thereof. The multilamellar liposomes comprise multilamellar vesicles of similar composition to unilamellar vesicles, but are prepared so as to result in a plurality of compartments in which the analogs containing solution or emulsion is entrapped. Additionally, other adjuvants and modifiers may be included in the liposomal formulation such as polyethyleneglycol, or other materials.

The liposomes containing the hepoxilin or hepoxilin analog compositions may also have modifications such as having antibodies immobilized on the surface of the liposome in order to target their delivery.

In one embodiment of the present invention is a pharmaceutical composition for administration to subjects in a biologically compatible form suitable for administration in vivo for treating a disorder associated with an increased level of thromboxane or a disorder wherein it is desirable to reduce thromboxane activity, including inflammatory disorders, thrombosis or diabetes and comprising a safe and effective amount of a hepoxilin or hepoxilin analog alone, or in combination with other agents and pharmaceutical carriers. The composition may be administered to any living organism in need of such treatment including humans and animals as the composition has efficacy in vivo. By safe and effective, as used herein, is meant providing sufficient potency in order to decrease, prevent, ameliorate or treat the disease affecting the subject while avoiding serious side effects. A safe and effective amount will vary depending on the age of the subject, the physical condition of the subject being treated, the severity of the disorder, the duration of treatment and the nature of any concurrent therapy, and its determination is within the skill of the ordinary physician.

A therapeutically active amount of a pharmaceutical composition of the present invention means an amount effective, at dosages and for periods of time necessary to achieve the desired result. This may also vary according to factors such as the disease state, age, sex, and weight of the subject and the ability of the hepoxilin or hepoxilin analog to elicit a desired response in the subject. Dosage regima may be adjusted to provide the optimum therapeutic response. For example, several divided doses may be administered daily or the dose may be proportionally reduced as indicated by the exigencies of the therapeutic situation.

By pharmaceutically acceptable carrier as used herein is meant one or more compatible solid or liquid delivery systems. Some examples include but are not limited to starches, sugars, cellulose and its derivatives, powdered tragacanth, malt, gelatin, collagen, talc, stearic acids, magnesium stearate, calcium sulfate, vegetable oils, polyols, agar, alginic acids, pyrogen free water, isotonic saline, phosphate buffer, and other suitable non-toxic substances used in pharmaceutical formulations. Other excipients such as wetting agents and lubricants, tableting agents, stabilizers, anti-oxidants and preservatives are also contemplated.

The compositions described herein can be prepared by known methods for the preparation of pharmaceutically acceptable compositions which can be administered to subjects, such that an effective quantity of the hepoxilin, hepoxilin analog or analogs is combined in a mixture with a pharmaceutically acceptable carrier. Suitable carriers are described for example in Remington's Pharmaceutical Sciences (Mack Publishing Company, Easton, Pa., USA, 1985). On this basis the compositions include, albeit not exclusively, solutions of the hepoxilin analog(s) in association with one or more pharmaceutically acceptable vehicles or diluents, and contained in buffered solutions with a suitable pH and iso-osmotic with the physiological fluids. Hepoxilin analogs may be prepared as described, for example, in U.S. Pat. No. 5,616,607.

EXAMPLES

The examples are described for the purposes of illustration and are not intended to limit the scope of the invention.

Methods of chemistry and biochemistry referred td but not explicitly described in this disclosure and examples are reported in the scientific literature and are well known to those skilled in the art.

Experimental Procedures

The following abbreviations are used: $TxB_2$, thromboxane $B_2$; HHT, 12-hydroxyheptadecatrienoic acid; ADAM, 9-anthryl esters; TLC, thin layer chromatography; HPLC, high performance liquid chromatography.

Materials

The hepoxilin analogs, PBT-1, -2, -3 and -4, were prepared as previously described (36); Collagen (Chrono-Par) was purchased from Chrono-log Corp., Havertown, Pa. ADAM reagent (9-anthryldiazomethane) was from Research Organics Inc., Cleveland, Ohio. Tritiated PGH2 and unlabeled $PGH_2$ were from Cayman Chemical, Ann Arbor, Mich. U46619 (5-heptenoic acid, 7-[6-(3-hydroxy-1-octenyl)-2-oxabicyclo-[2,2,1]-hept-5yl]-[1R-[1$\alpha$,4$\alpha$,5$\beta$(z), 6$\alpha$(1E, 3S*)]-9,11-dideoxy-9$\alpha$,11$\alpha$-methanoepoxy prostaglandin $F_{2\alpha}$), I-BOP (5-heptenoic acid, 7-[3-[3-hydroxy-4-(4-iodophenoxy)-1-butenyl]-7-oxabicyclo [2.2.1]hept-2-yl]-,[15-[1$\alpha$, 2$\alpha$(Z), 3$\beta$(1E,3S*), 4$\alpha$]]) and $^{125}$I-BOP were from Cayman Chemicals, Ann Arbor, Mich., U.S.A.

Preparation of Human Platelets

Venous blood was obtained from healthy human subjects who had not taken NSAID's for at least two weeks. Blood was drawn into plastic syringes containing ACD. It was immediately centrifuged at 23° at 200×g for 15 min. The platelet rich plasma was transferred into fresh plastic tubes and centrifuged at 400×g for 5 min. The supernatant was discarded and the platelet sediment was resuspended in fresh medium containing NaCl (137 mM), KCl (1 mM), $NaH_2PO_4$, glucose (5.5 mM), HEPES (20 mM) and $CaCl_2$ (1 mM) and allowed to stand at room temperature for 30 min. A platelet count was made, which determined the volume of platelet suspension needed to make up $350 \times 10^6$ cells for each measurement. The aliquot was diluted with medium to make 0.5 ml/assay/cuvette. Appropriate calibration of the aggregometer (PAP-4C) for 0% and 100% transmission was carried out through the use of a sample of platelet suspension and cell-free medium (37).

Platelet Aggregation and Sample Extraction 0.5 ml of platelet suspension was added to siliconized glass tubes (four at a time) and heated with magnetic stirring to 37° for 1 min in a platelet aggregometer (PAP-4C). Either vehicle alone (ethanol, 1 μl) or hepoxilin analog was then added, followed two min later by agonist (collagen: 2 μg; $PGH_2$: 100 ng/0.5 ml; U46619: 10 ng/0.5 ml or I-BOP: 2 ng/0.5 ml). The response was recorded for the next 5 min. In experiments where analysis of $TxB_2$ and HHT were to be made by HPLC, the platelet suspension at the end of the experiment was diluted with ethyl acetate, 100 ng of prostaglandin $B_1$ was added as internal standard, and the mixture was acidified to pH 3 with 0.1 N HCl. After centrifugation, the organic layer was separated, washed twice with water to neutrality, and evaporated to dryness. Half of the sample was taken and was resuspended in 1 ml ethyl acetate containing 20 μg ADAM reagent, and was left in the dark for 2 h (38). The solvent was then evaporated and the residue was acetylated with a solution of pyridine/acetic anhydride (3/1, v/v) during 16 h at 23°. The reagents were evaporated to dryness and the residue was resuspended in acetonitrile/water for HPLC analysis. In experiments where the conversion of tritiated $PGH_2$ was to be monitored, the procedure described above was repeated with tritiated $PGH_2$ instead of unlabeled $PGH_2$. After extraction of the sample as described above, the radiolabeled compounds were analyzed by TLC. Dose response curves for varying amounts of test compounds were generated and the data expressed as % inhibition of collagen-induced platelet aggregation. Each point was investigated 5 times and statistical analysis of the data was carried out using Macintosh Statview statistical software.

In experiments addressing whether levels of endogenously produced thromboxane A2 play a role in the inhibition of aggregation by PBT-3, platelets were treated with aspirin (20 µg/0.5 ml), followed either by collagen or the thromboxane agonists, I-BOP or U46619; PBT-3 was added, post aspirin but pre-I-BOP or U46619.

Binding of $^{125}$I-BOP to Platelets

Washed platelets were prepared as described above, except that the platelet suspension was made up at a concentration of $10 \times 10^6$ cells/0.5 ml. The binding assay involved the addition of radioligand (30,000 cpm $^{125}$I-BOP) to all tubes in triplicate, and either various doses of unlabeled I-BOP ($10^{-9}$-$10^{-7}$ M), PBT-3 ($10^{-9}$-$10^{-7}$ M) or U46619 ($10^{-9}$-$10^{-7}$ M) in 1 µl ethanol. Additional tubes containing excess unlabeled I-BOP were included to assess the extent of non-specific binding.

Measurement of COX-1 and COX-2 Activity

COX-1 and COX-2 enzyme preparations were purchased from Cayman Chemicals. Preliminary studies established that 40 U of COX-1 or COX-2 could convert about 70% of $^{14}$C-arachidonic acid (spec. act. 55 mCi/mmol, Ontario Isotopes, Ontario, Canada; 100,000 cpm were diluted with 0.5 µg unlabeled arachidonic acid (Cayman Chemicals)/1 ml assay) into products in vitro. Different amounts of PBT-3 (10 µg and 20 µg) were added and the conversion of AA into products was assessed during a 10 min reaction in 1 ml phosphate buffer at 37°. After extraction, products were assessed by TLC (silica gel G, ethyl acetate/acetic acid, 99/1, v/v). After development, the TLC plates were scanned for radioactive products with a Berthold TLC radiochromatogram scanner and the radioactivity was quantified by scraping zones of silica gel, placing in scintillation vials, elution with 1 ml methanol and addition of scintillation medium. Radioactivity was determined by conventional counting in a beta scintillation counter.

Measurements of Platelet Derived Eicosanoids

Measurement of eicosanoids formed by platelets during treatment with collagen or the TP receptor agonists in the presence or absence of PBT-3 was carried out by HPLC after appropriate derivatization with a fluorescent tag (anthracyl diazomethane—ADAM) which forms a fluorescent ester (44). The method was adapted to measure the following compounds: TxB2, HHT, 12-HETE and M. The platelet suspension at the end of the experiment was mixed with ethyl acetate, 100 ng of prostaglandin $B_1$ was added as internal standard and the mixture was acidified to pH 3 with 0.1 N HCl. After centrifugation, the organic layer was separated, washed twice with water to neutrality, and evaporated to dryness. The residue was resuspended in ethyl acetate and half of the sample was taken. It was diluted to 0.2 ml with ethyl acetate containing 20 µg ADAM reagent, and was left in the dark for 2 h. The solvent was then evaporated and the residue was acetylated with a solution of pyridine/acetic anhydride (3/1, v/v) for 16 h at 23°. The reagents were evaporated to dryness and the residue was resuspended in acetonitrile/water for HPLC analysis. Dose response curves for varying amounts of test compounds were generated and the data were expressed as % inhibition of agonist-induced platelet aggregation. Each point was investigated 3 times and statistical analysis of the data was carried out using Macintosh Statview statistical software.

Chromatography

Analysis of the anthryl (ADAM)-acetate derivative of $TxB_2$, HHT and 12 HETE in the extracted platelet samples was carried out on a Hewlett Packard (1100 series) HPLC to which was attached a Shimadzu fluorescent detector (RF-10AXL). The detector was operated with excitation at 364 nm, emission at 411 nm. Chromatographic separation of the compound was carried out on a Waters C18 Novapak column (3.9×300 mm) using acetonitrile/water 80/20 at injection with a linear gradient to 100% acetonitrile during 20 min. TLC separation of tritiated platelet extracts was carried out on 20 cm silica gel G glass plates (Brinkman), with chloroform/methanol/acetic acid/water (90/9/1/0.65, v/v) as developing solvent in a paper lined glass tank at 23°. After development, the radioactive products were detected by scanning the TLC plate on a Berthold TLC radiochromatogram scanner.

Statistical Analysis

Values shown are the mean±SD of the number of observations (n) indicated. Analysis of statistical significance was performed using Student t-test involving Macintosh Statview software program.

Example 1

Four hepoxilin analogs (the methyl esters PBT-1, -2, -3 and -4) were tested for inhibition of collagen-evoked aggregation of washed human platelet suspensions. FIG. 1 compares the effects of these compounds at a single dose (1 µg) added 2 min prior to the addition of a pro-aggregatory dose of collagen (2 µg). All four analogs inhibited the collagen effect, with PBT-3 being the most potent.

FIG. 2 shows the dose response curves of the four compounds in this study. The IC50 for the most active compound, PBT-3, was approx. $8 \times 10^{-7}$ M. Native hepoxilins were less active than the analogs.

The galactose amide and galactose ester derivatives corresponding to PBT-1, -2, -3 and 4 were also tested and were found to inhibit collagen-evoked platelet aggregation (data not shown).

Example 2

In order to determine whether the hepoxilin analogs affect $TxA_2$ formation (measured as the stable degradation product TxB2), experiments were set up in which the contents of the cuvettes from aggregation experiments as described above were extracted for $TxB_2$ and analyzed by HPLC after appropriate derivatization of the samples for fluorescence detection. The results are shown in FIG. 3. $TxB_2$ formation was inhibited in a dose-dependent manner by the four analogs, again to a greater extent by PBT-3. The $IC_{50}$ for inhibition of TxB2 formation was in the same range as that for inhibition of platelet aggregation.

Example 3

Additional experiments were set up to directly monitor the inhibitory effects of PBT-3 on thromboxane formation. $PGH_2$ is converted into $TxB_2$ by platelets. As shown in FIG. 4, $PGH_2$ at 100 ng caused platelets to aggregate. Addition of PBT-3 at various doses before addition of $PGH_2$ inhibited the second wave of aggregation which is known to be evoked by formation of TxA$_2$, a potent pro-aggregating substance. This is additional confirmation that PBT-3 inhibited TxA$_2$ formation.

Example 4

Tritiated PGH$_2$ was employed to confirm its conversion into TxB$_2$ by platelet suspensions and the inhibition of this formation of TxA$_2$ by PBT-3. FIG. 5 shows a TLC profile demonstrating the inhibitory action of two doses of PBT-3 on TxB2 formation (as a measure of the bioactive product TxA$_2$).

Example 5

Additional experiments were set up to test the actions of the hepoxilin analogs on platelet aggregation evoked by the TxA$_2$ mimic, U46619, working through the TP receptor. The methods were as in Example 3, but instead of collagen, U46619 was added to evoke aggregation. PBT-3 at a dose of 1 µg inhibited the aggregation by U46619 (FIG. 6).

Example 6

Dose related aggregation curves for I-BOP, a potent thromboxane receptor agonist, indicated that at a concentration of 2 ng/0.5 ml, it caused 70% aggregation (data not shown). This dose was therefore chosen as it represented a point at which inhibition curves for the test compounds could be most sensitive (FIG. 7A). Addition of PBT-3 2 minutes prior to I-BOP caused a pronounced inhibition of I-BOP-induced aggregation in a dose related fashion. FIG. 7A shows aggregation responses in human washed platelet suspensions evoked by I-BOP and the inhibition of this response by different doses of PBT-3 added 2 min prior to the addition of I-BOP. FIG. 7B shows aggregation responses of human washed platelets challenged with U46619 and their inhibition by different amounts of PBT-3. FIG. 8 provides quantitative data for these experiments demonstrating an IC$_{50}$ for inhibition of aggregation evoked by I-BOP at $0.6 \times 10^{-7}$ M of PBT-3. PBT-3 also inhibited the aggregation evoked by the agonist, U46619 with an IC$_{50}$ of $7 \times 10^{-7}$ M demonstrating the greater selectivity of PBT-3 for I-BOP versus U46619 (FIG. 8). Collagen evokes the aggregation of human platelets through the formation of thromboxane A$_2$. PBT-3 dose dependently prevented collagen-evoked aggregation of platelets with an IC$_{50}$ of $8 \times 10^{-7}$ M. Analysis of the thromboxane formed in these experiments indicated that collagen-evoked formation of thromboxane was blocked by PBT-3 with an IC$_{50}$ of $8 \times 10^{-7}$ M. In separate studies (data not shown) it was demonstrated that I-BOP-evoked or U46619-evoked aggregation was not accompanied by thromboxane formation; hence PBT-3 inhibition of the action of these two thromboxane mimetics is due to direct inhibition at the TP receptor level and was not dependent on endogenous formation (or blockade) of thromboxane A$_2$.

Example 7

The binding of $^{125}$I-BOP to platelets was examined, as Well as the competition of I-BOP, PBT-3 and U46619 with this binding. FIG. 9 shows that PBT-3 competed with the binding of $^{125}$I-BOP to platelets in a dose dependent way. Competition curves are shown for I-BOP (IC$_{50}$ $0.5 \times 10^{-9}$ M), PBT-3 (IC$_{50}$=$8.1 \times 10^{-9}$ M) and U46619 (IC$_{50}$=$4.1 \times 10^{-9}$ M). PBT-3 was about 16 fold less active than I-BOP in competing with $^{125}$I-BOP binding to the platelet TP receptor, but was of similar activity to U46619:

Example 8

To establish whether inhibition of endogenous formation of thromboxane plays a role in the inhibitory effect of PBT-3 on the platelet aggregation process, rather than antagonism of thromboxane action at the TP receptor, experiments were carried out in which platelets were treated with aspirin (to block endogenous thromboxane formation) followed by the agonist, U46619 (which causes aggregation even after aspirin treatment). FIG. 10 shows an aggregation profile of such an experiment. Both collagen and U46619 caused platelets to aggregate—see FIG. 10, lines 1 and 2 respectively. Aspirin greatly reduced collagen-evoked aggregation (FIG. 10—early part of line 3). A dose of 20 µg aspirin was employed for this study, as this dose blocked collagen effects almost completely (data not shown), demonstrating that collagen-induced platelet aggregation is mediated through the formation of endogenous thromboxane. In contrast, aspirin at this dose did not block U46619-evoked aggregation (FIG. 10—later part of line 3) demonstrating that aspirin did not interfere with the TP receptor or the cascade of events initiated by U46619. Addition of PBT-3 to aspirin-treated platelets before the addition of U46619 resulted in a blockade of the aggregation induced by U46619 (FIG. 10—line 4, compare with line 3). This confirmed that PBT-3 caused inhibition of the action of U46619 at the TP receptor level, independently of its effects on the formation of endogenous thromboxane.

Example 9

Several experiments were carried out to investigate whether PBT-3 affected several enzymes involved in the generation of various eicosanoids, or whether it acted to block selectively thromboxane formation subsequent to its actions at the TP receptor. The data are summarized in Table 1. Neither COX-1, COX-2,12-LOX nor Plase A2 was inhibited by relatively large amounts of PBT-3, i.e. about 3-4 log doses greater than that required to inhibit the TP receptor. In contrast, PBT-3 significantly inhibited TxB2 formation in platelets (Table 1, last column).

Example 10

Brown Norway rats (300 g) were purchased from Charles River (St. Constant, Que), and housed (two/cage) in an animal facility with free access to food and water. A light cycle of 12 h on and 12 h off was maintained. Animals were allowed to adjust for one week prior to treatment during which period they were handled daily to get them familiarized with the procedures.

Prior to treatment with test drugs, the rats' intra ocular pressures (IOP) were measured to establish baseline readings. One drop of Didocaine (0.5%, Dioptic Labs, Markham, Ont) was administered to each eye, and the pressure in each eye was measured with a TonoPen (Mentor XL, Innova Medical Ophthalmics, Toronto). The treatment protocol consisted of daily administration of one drop of one of the following substances to the left eye, the right eye being left untreated to act as a control. Each animal received one of the following treatments daily for three weeks: Ophtho-bunolol (0.5%)+latanoprost (Xalatan) (0.005%), latanoprost (0.005%), normal saline, PBT-3 in saline (0.005%), PBT-30 (10(S)-hydroxy-11,12-cyclopropyl-eicosa-5Z, 8Z, 14Z-trienoic acid galactosamide) in saline (0.005%), or Ophtho-bunolol (0.5%). IOP was measured weekly. Following this, the animals were left without treatment for 2 weeks (wash-out), and then treatment was started again, the same animals receiving the same drugs. Results are calculated from at least 30 readings/test animal and presented as the mean±SEM (left eye vs right eye), with the exclusion of readings >50 and <10 which were considered spurious and artifactual readings.

FIG. 11 is representative of one measurement point after 10 days' treatment. While latanoprost gave a significant reduction in IOP, O-bunolol gave a non-significant rise, which is also reflected in a reduced effect of the combination of latanoprost and O-bunolol. PBT-3 gave a significant reduction in IOP, comparable to that produced by latanoprost. PBT-30 also tended to reduce IOP but the effect did not reach statistical significance at the dose tested.

Saline, the vehicle for the PBT compounds, caused an increase in IOP relative to the untreated eye (data not shown).

Example 11

Galactose amides of hepoxilin analogs were prepared as follows.

All solvents were glass distilled and used as obtained (Caledon, Georgetown, Ontario). 1-(3-dimethylaminopropyl)-3-ethylcarbodiimide (DMAPEC), N-hydroxysuccinimide and D-galactosamine.HCl were obtained from Aldrich Chemicals (USA).

8(S)-hydroxy-11,12-cyclopropyl-eicosa-5Z, 9E, 14Z-trienoic methyl ester (compound (1) of FIG. 12) was prepared as described previously in U.S. Pat. No. 5,616,607. The corresponding free acid was prepared by conventional hydrolysis of the methyl ester, in NaOH/ethanol for 30 minutes at 23° and extraction with ethyl acetate after acidification. The resulting free acid was purified by HPLC by conventional techniques and subjected to activation as described below.

30 µmol of the free acid was coupled, through the free carboxyl group, with N-hydroxysuccinimide (220 µmol) in methylene chloride. Finely ground activated molecular sieves (3A) were added, followed by the addition of 220 µmol of DMAPEC. The reaction mixture was stirred for 3 h at 20°, the molecular sieves were filtered off, and the solution was washed with water (3×2 ml) and taken to dryness. The residue was purified by preparative RP-HPLC (Nova-Pak C18 column (Waters), 3.9×300 mm, eluent acetonitrile-water, 70:30, flow rate 1.5 ml/min, UV detector at 205 nm) and the fraction with retention time 5.0-5.2 minutes was collected. After evaporating the solvents, a colourless oil was obtained with a yield of approximately 89-93%. Electrospray mass spectrometry (API III Plus triple quadrupole with direct injection) was done to confirm the structure of the N-hydroxy succinimide ester (compound (2) of FIG. 12) with $[M+NH_4]^+$ at 449 (100% intensity).

The N-hydroxysuccinimide ester (28 µmol) was then dissolved in 1,4-dioxane. A solution of 140 µmol of D-galactosamine.HCl and 180 µmol of $NaHCO_3$ in water was added, and the mixture was allowed to stand for 4 h at 200. The solvents were taken to dryness and the residue was purified by preparative RP-HPLC (acetonitrile-water, 50:50; flow rate 1.0 ml/min). The fraction between 7.0-7.5 minutes was collected. After evaporating the solvents, white crystals were obtained with a yield of approximately 79-83%. The structure was confirmed by NMR and mass spectrometry (m/z 513 $[M+NH_4]^+$; 100% intensity).

Example 12

Synthesis of 1,2,3,4-tetra(2,6-di-O-tert-butyldimethylsilyl) protected galactose intermediate (1)

Galactose esters of hepoxilins and hepoxilin analogs were synthesised as described in Demin et al. (45), and as described briefly below. The general synthetic scheme is shown in FIGS. 13 and 14.

To obtain the 1,2,3,4-tetraBDMS (1,2,3,4-tetra(2,6-di-O-tert-butyldimethylsilyl)) protected galactose 1 (FIG. 13), diisopropylidene protected galactose 2 was acetylated to yield compound 3, followed by acetonide deprotection of compound 3 with 90% TFA in water to yield 6-acetyl galactose 4. 6-acetyl galactose 4 was silylated using BDMSCI-imidazole-DMF. Basic hydrolysis of the obtained 6-acetate 5 led to the target crystalline material, 1,2,3,4-tetra-O-(tert-butyldimethylsilyl)-D-galactopyranose 1, obtained as a mixture of α- and β-anomers (FIG. 13).

1,2:3,4-Di-O-isopropylidene-6-acetyl-α-D-galactopyranose (3)

To 520 mg (2.0 mmol) of 1,2:3,4-Di-O-isopropylidene-D-galactopyranose 2 ($R_f$ 0.06, EtOAc-hexane, 1:2) 2.0 mL pyridine and 1.5 mL acetic anhydride were added. The reaction mixture was kept at 60° C. for 3 h and the reagents were removed with a stream of nitrogen. The yield of 6-acetate 3 was 580 mg (96%). $R_f$ 0.22, EtOAc-hexane, 1:2. The compound was used without further purification. Distillation on a kugelrohr apparatus at an oven temperature of 120° C. and under a 0.1 mm Hg vacuum gave an analytical sample as a viscous oil.

$[\alpha]_D^{25}$ -47° (c 1.0, $CHCl_3$). $^1$H-NMR ($CDCl_3$, δ, ppm): 1.34, 1.45, 1.52, 1.59 (4×s, 12H, isopropylidene), 2.09 (s, 3H, OAc), 4.03 (m, 1H, $H^5$), 4.19 (dd, 1H, J 7.5 and 11.5 Hz, $H^6$), 4.24 (br. d, 1H, J 7.9 Hz, $H^4$), 4.29 (dd, 1H, J 4.9 and 11.5 Hz, $H^{6'}$), 4.33 (dd, 1H, J 2.3 and 4.9 Hz, $H^2$), 4.62 (dd, 1H, J 2.3 and 7.9 Hz, $H^3$), 5.54 (d, 1H, J 4.9 Hz, $H^1$). MS (m/e, relative intensity, %): 303 ($[M+H]^+$, 100), 320 ($M+NH_4]^+$, 97).

6-Acetyl-α,β-D-galactopyranose (4)

To 580 mg (1.92 mmol) of 1,2:3,4-Di-O-isopropylidene-6-acetyl-D-galactopyranose 3 2.0 mL of 90% trifluoroacetic acid was added. The reaction mixture was kept at 20° C. for 15 min and the reagents were removed with a stream of $N_2$ followed by azeotropic evaporation of traces of water with acetonitrile (3×20 mL). The yield of 6-acetyl-D-galactopyranose 4 was 392 mg (92%). The compound was crystallized from 5% MeOH in MeCN, m.p. 139-141° C. (lit$^i$, m.p. 130-132° C.).

$[\alpha]_D^{25}$ +91° (c 1.0, $H_2O$) (lit$^i$, $[\alpha]_D^{25}$ +95.6° (c 1.0, MeOH). MS (m/e, relative intensity, %): 204 ($[M-H_2O]^+$, 60), 223 ($[M+H]^+$, 33), 240 ($[M+NH_4]^+$, 100).

1,2,3,4-Tetra-O-(t-butyldimethylsilyl)-6-acetyl-α,β-D-galactopyranose (5)

6-Acetyl-D-galactopyranose 4 (392 mg, 1.76 mmol) was dissolved in 30 mL DMF. t-BDMSCI (1590 mg, 10.56 mmol)

and imidazole (1440 mg, 21.12 mmol) were added. The reaction mixture was stirred at 50° C. for 12 h, poured into 200 mL of water and extracted with hexane (3×50 mL). The hexane fractions were dried with $Na_2SO_4$ and evaporated. The residue was distilled on a Kugelrohr apparatus at 0.01 mm Hg, collecting a fraction at an oven temperature of 170-180° C. The obtained colorless oil was purified by column chromatography on silica gel, eluent 2-5% EtOAc in hexane, and the target fraction was collected ($R_f$ 0.63, EtOAc-hexane, 1:2). After evaporation a viscous oil 5 was obtained (780 mg, 65%).

$[\alpha]_D^{25}$ −40° (c 0.5, $CHCl_3$). $^1$H-NMR ($CDCl_3$, δ, ppm): 0.09, 0.90 (2×m, 60H, Si$^t$Bu and SiMe$_2$), 2.05 (s, 3H, OAc), 3.90-4.03 (m, 5H, $H^{2+4+5+6+6'}$), 4.17 (dd, 1H, J 3.9 and 11.4 Hz, $H^3$), 5.14 (br. s., 1H, $H^1$). MS (m/e, relative intensity, %): 547 ([M+H−BDMSOH]$^+$, 100), 679 ([M+H]$^+$, 51), 696 ([M+NH$_4$]$^+$, 82).

1,2,3,4-Tetra-O-(tert-butyldimethylsilyl)-α,β-D-galactopyranose (1)

1,2,3,4-Tetra-O-(tert-butyldimethylsilyl)-6-acetyl-D-galactopyranose 5 (460 mg, 0.68 mmol) was dissolved in 150 mL THF-MeOH, 1:1. 20 mL 1 N NaOH was added and the reaction mixture was stirred for 8 h at 20° C. The organic solvents were evaporated, 200 mL of saturated NaCl solution was added and the mixture was extracted with benzene (4×100 mL). The organic layers were combined and dried with $Na_2SO_4$, taken to dryness and purified by column chromatography on silica gel using 2-20% EtOAc in hexane as the eluent. The fraction with $R_f$ 0.47 (EtOAc-hexane, 1:2) was collected. After evaporation the target compound 1 (crystals, 337 mg, 78%) was obtained. The analytical sample was crystallized from hexane at −70° C. giving white needle-shape crystals, m.p. 130-132° C.

$[\alpha]_D^{25}$ −57° (c 1.0, $CHCl_3$). $^1$H-NMR ($CDCl_3$, δ, ppm): 0.11, 0.90 (2×m, 60H, Si$^t$Bu and SiMe$_2$), 3.64 (dd, 1H, J 5.1 and 9.8 Hz, $H^4$), 3.70 (dd, 1H, J 1.7 and 9.8 Hz, $H^3$), 3.78 (m, 1H, $H^5$), 3.85 (br. s, 1H, $H^2$), 4.06, 4.13 (2×m, 2H, $H^{6+6'}$), 5.28 (br. s, 1H, $H^1$). MS (m/e, relative intensity, %): 523 ([M+H−BDMSOH+NH$_4$]$^+$, 55), 540 ([M−BDMSOH+NH$_4$+NH$_4$]$^+$, 100), 637 ([M+H]$^+$, 3.7), 654 ([M+NH$_4$]$^+$, 4.5).

Synthesis of Galactose Esters of Hepoxilins

As shown in FIG. 14, 1,2,3,4-Tetra-O-(tert-butyldimethylsilyl)-α,β-D-galactopyranose 1 is reacted with 8 or 10-BDMS protected hepoxilins 7a,b in the presence of EDAC/DMAP (1-(3-dimethylaminopropyl)-3-ethylcarbodiimide hydrochloride (EDAC)/4-dimethylaminopyridine (DMAP)) to give the hepoxilinyl esters of tetraBDMS galactose 8a,b. The anomers of tetraBDMS galactose fatty esters 8a,b were separable both by TLC and HPLC. The treatment of the compounds 8a,b with equimolar amounts of n-Bu$_4$NF, Py.HCl, THF gave the target compounds 9a,b. Both α- and β-anomers of the hepoxilin esters 8a,b led to the same products 9a,b after deprotection. RP-HPLC analysis of the products 9a,b showed a poorly separated doublet, corresponding to the mutarotating α- and β-anomers (FIG. 13).

8 or 10-tert-Butyldimethylsilyl-8 or 10S/R-delta-HxA$_3$ and delta-HxB$_3$ (7a$_{s,r}$, 7b$_{s,r}$)

To 4 mg (11.5 μmol) of the corresponding delta-Hx methyl ester, a solution of 15 mg (100 μmol) of t-butyldimethylchlorosilane and 13.6 mg (200 μmol) of imidazole in 100 μl DMF was added. The mixture was kept at 50° C. for 0.5 h, 5 mL of water was added and the mixture was extracted with hexane (3×2 mL). After removing the hexane from the organic layer, the residue was purified by RP-HPLC (column 3.9×300 mm, 100% MeCN, flow rate 2.0 mL/min). The fraction having a retention time of 6.5 min was collected. A colorless oil was obtained after evaporation of the solvent. The yield of the 8 or 10-tert-butyldimethylsilyl derivatives of delta-Hx methyl esters was 5.3 mg (100%). The methyl esters were hydrolyzed to 8/10-tert-butyldimethylsilyl-(8/10R/S)-delta-HxA$_3$/B$_3$ (MeOH-1N NaOH, 2:1, 4 h, RT). After acidification to pH 4, the mixture was extracted with EtOAc and passed through silica gel using EtOAc as the eluent. After evaporation the yield of BDMS-derivatives of delta-Hx 7a,b was 5.15 mg (100% after two steps).

1,2,3,4-Tetra-O-(t-butyldimethylsilyl)-6-[8 or 10-t-butyldimethylsilyl]delta-[8 or 10S/R]-hepoxilin A$_3$(B$_3$)-yl-α,β-D-galactopyrahoses (8a$_{s,r}$, 8b$_{b,r}$)

5.15 mg (11.5 μmol) of 10-BDMS derivatives of delta-Hx 7a,b in 3 mL $CH_2Cl_2$ were treated with 10.9 mg (17.3 μmol) of tetra-O-(t-butyldimethylsilyl)-D-galactopyranose 1, 6.6 mg (34.5 μmol) of EDAC and 0.1 mg of DMAP for 24 h at 20° C. HPLC analysis (column 3.9×75 mm, 100% MeCN, flow rate 5.0 mL/min) showed two peaks in a 1:1 ratio, and retention times 11.6 and 14.6 min corresponding to the α- and β-anomers. The mixture was washed with water (2×2 mL), taken to dryness and purified by RP-HPLC in the same system, collecting both α- and β-anomers as a single fraction. Total yield 9.9-10.1 mg (80-82%).

$^1$H-NMR ($CDCl_3$, δ, ppm), 8a$_s$, 8a$_r$ (identical to each other, see also ref.[5]): 0.53 (m, 2H, cyclopropyl), 0.76, 1.16 (2×m, 2×1H, $H^{11}$ and $H^{12}$ in the fatty chain), 4.02 (dt, 1H, J 6.1 and 6.4 Hz, $H^8$ in the fatty chain), 5.23, 5.25 (2×br. s, 2×0.5H, $H^{1\alpha}$ and $H^{1\beta}$); 0.10, 0.90 (BDMS); 0.90, 1.27-1.38, 1.70, 2.01, 2.06, 2.20, 2.33, 5.37-5.45 (fatty chain moiety); 3.61, 3.67-3.76, 3.80, 3.86, 3.96, 4.14, 4.23, 4.84, 5.09, 5.14 (α- and β-galactose moiety). 8b$_s$: identical to 8a$_s$, 8a$_r$ except the following: 0.23, 0.41 (2×m, 2×1H, cyclopropyl), 0.71-0.80 (m, 2H, $H^{11+12}$ in the fatty chain), 3.97 (m, 1H, $H^{10}$). 8b$_r$: identical to 8b$_s$ except the following: 3.86 (m, 1H, $H^{10}$). MS (either regio/stereoisomer, m/e, relative intensity, %): 970 ([M−BDMSOH+NH$_4$+NH$_4$]$^+$, 100)

6-(8 or 10S/R)-Hepoxilin A$_3$(B$_3$)-yl-α,β-D-galactopyranoses (9a$_{s,r}$, 9b$_{s,r}$)

to 3 mg (2.81 μmol) of the compounds 8a,b in 300 μl of freshly distilled THF, 40 μl of 0.5M Py.HCl in THF-5% $H_2O$ was added, followed by 20 μl of 1 M n-Bu$_4$NF in THF. The mixture was allowed to stand for 0.5 h at 20° C., the THF was removed, and the residue was purified by RP-HPLC (column 3.9×300 mm, MeCN—$H_2O$, 60:40, flow rate 1.0 mL/min). The doublet of peaks at retention times 6.0-7.0 min was collected. The yield was 1.10 mg (79%). MS (either regio/stereoisomer, m/e, relative intensity, %): 461 ([M+H—$H_2O$—$H_2O$]+), 479 (M+H—$H_2O$]$^+$), 514 ([M+NH$_4$]$^+$, 100).

TABLE 1

Effect of PBT-3 on various enzyme systems related to arachidonic acid metabolism

| Concentration of PBT-3 (μM) | COX-1* | COX-2* | Plase $A_2^+$ | 12-LOX$^+$ | TX |
|---|---|---|---|---|---|
| 30.0 | $116.8 \pm 11^{NS}$ | $107.1 \pm 14^{NS}$ | ND | ND | ND |
| 3.00 | $119.6 \pm 14^{NS}$ | $109.2 \pm 8.0^{NS}$ | $120.8 \pm 18.3^{NS}$ | $102.5 \pm 5.7^{NS}$ | $29.9 \pm 6.7**$ |
| 0.60 | ND | ND | $89.5 \pm 15.6^{NS}$ | $73.0 \pm 4.9**$ | $41.0 \pm 4.7**$ |
| 0.30 | ND | ND | $91.9 \pm 5.6^{NS}$ | $85.2 \pm 7.4^{NS}$ | $65.7 \pm 6.0*$ |
| 0.05 | ND | ND | $100.0 \pm 6.9^{NS}$ | $79.4 \pm 7.6*$ | $94.2 \pm 15.2^{NS}$ |

Enzyme activity (n = 3) (% of control values, mean ± SD)

*calculated from the percent of $^{14}$C-AA remaining from TLC analysis of incubation of 40 Units of COX-1 or 20 Units of COX-2 (10 min, 37°) with $^{14}$C-AA (see Methods for details). Under these conditions, in control experiments (without PBT-3) the amount of AA remaining at the end of the experiment was approximately 30%, the rest being converted into polar products including HETEs and prostaglandins.
$^+$calculations, from HPLC analysis, of the amount of AA (Plase $A_2$), 12-HETE (12-LOX), TxB$_2$ and HHT (TX synthase) formed during incubation of washed human platelets treated with collagen ± PBT-3 (6 min, 37°) and expressed as percent of collagen-stimulated controls (in the absence of PBT-3)(see Methods for details)
*= 0.01 < p < 0.025,
**= 0.0005 < p < 0.01,
***= p < 0.0005,
NS = p > 0.025,
ND = not determined

REFERENCES

1. Hamberg, M., Svensson, J., and Samuelsson, B. (1975) Proc. Natl. Acad. Sci. USA 72, 2994-2998.
2. Hamberg, M., and Samuelsson, B. (1974) Proc. Natl. Acad. Sci. USA 71, 3400-3404.
3. Diczfalusy, U., and Hammarstrom, S. (1980) Biochem. Biophys. Res. Commun. 94, 1417-1423.
4. Hammarstrom, S., and Diczfalusy, U. (1980) Advances in Prostaglandin and Thromboxane Research 6, 267-274.
5. Fu, Z. Z., Yan, T., Chen, Y. J., and Sang, J. Q. (1992) Metabolism 41, 33-35.
6. Hendra, T., and Betteridge, D. J. (1989) Prostagl. Leuk. Essen. Fatty Acids. 35, 197-212.
7. Webster, J., Porta, M., Hensby, C. N., Kohner, E. M., MacDermot, J., and Lewis, P. J. (1981) Clin. Pharmacol. Prostacyclin, 113.
8. Fitzgerald, D. J., Rocki, W., Murray, R., Mayo, G., and FitzGerald, G. A. (1990) Lancet 335, 751-754.
9. Himmelstein, S. I., and Klotman, P. E. (1989) Am. J. Physiol. 257, F190-F196.
10. Lëscher, T. F. (1990) Am. J. Hypertens. 3, 317-330.
11. Minuz, P., Barrow, S. E., Cockcroft, J. R., and Ritter, J. M. (1990) Hypertension 15, 469-474.
12. Purkerson, M., Martin, K., Yates, J., and Klahr, S. (1985) Meeting Of The American Society Of Nephrology, Washington, D.C. USA.
13. Yamashita, W., Ito, Y., Ooi, B. S., and Pollak, V. E. (1986) Forty-third Annual National Meeting Of The American Federation For Clinical Research Washington, D.C.—USA.
14. Fiedler, V. B., Perzborn, E., Seuter, F., Rosentreter, U., and Böshagen, H. (1.989) Arzneimittelforschung 39, 1527-1530.
15. Parellada, P. P., and Planas, J. M. (1977) Lancet, 40.
16. Randall, M. J., and Wilding, R. I. R. (1982) Thromb. Res. 28, 607-616.
17. Silver, R. M., Edwin, S. S., Trautman, M. S., Simmons, D. L., Branch, D. W., Dudley, D. J., and Mitchell, M. D. (1995) J. Clin. Invest. 95, 725-731.
18. Zaitsu, M., Hamasaki, Y., Matsuo, M., Miyazaki, M., Hayasaki, R., Muro, E., Yamamoto, S., Kobayashi, I., Ichimaru, T., and Miyazaki, S. (1999) Eur. J. Haematol. 63, 94-102.
19. Wolkow, P. P., Bartus, J. B., and Gryglewski, R. J. (1997) J. Physiol. Pharmacol. 48, 645-653.
20. Coleman, R. A., Humphrey, P. P. A., Kennedy, I., and al., e. (1981) Br. J. Pharmacol. 73, 773-778.
21. Pollock, W. K., Armstrong, R. A., Brydon, L. J., Jones, R. L., and MacIntyre, D. E. (1984) Biochem. J. 219, 833-842.
22. Tymkewycz, P. M., Jones, R. L., Wilson, N. H., and Marr, C. G. (1991) Br. J. Pharmacol. 102, 607-614.
23. Heidemann, S. M., and Sarnaik, A. P. (1997) Prostagl. Leuk. Essen. Fafty Acids 56, 473-478.
24. Kamijo, T., Yamamoto, R., Harada, H., and Iizuka, K. (1983) Chem. Pharm. Bull. (Tokyo) 31, 1213-1221.
25. Pace-Asciak, C. R., Reynaud, D., Demin, P., and Nigam, S. (1999) In: Lipoxygenases and Their Metabolites—Biological Functions. Advances in Experimental Medicine and Biology, Vol: 447, Eds. S. Nigam and C. R. Pace-Asciak, Kluwer Academic/Plenum Publishers, New York, pp. 123-132.
26. Pace-Asciak, C. R. (1994) Biochim. Biophys. Acta 1215, 1-8.
27. Pace-Asciak, C. R., Reynaud, D., and Demin, P. M. (1995) Lipids 30, 1-8.
28. Laneuville, O., Reynaud, D., Grinstein, S., Nigam, S., and Pace-Asciak, C. R. (1993) Biochem. J. 295, 393-397.
29. Dho, S., Grinstein, S., Corey, E. J., Su, W. G., and Pace-Asciak, C. R. (1990) Biochem. J. 266, 63-68.
30. Reynaud, D., Demin, P., and Pace-Asciak, C. R. (1996) Biochem. J. 313, 537-541.
31. Margalit, A., Sofer, Y., Grossman, S., Reynaud, D., Pace-Asciak, C. R., and Livne, A. (1993) Proc. Natl. Acad. Sci. (USA) 90, 2589-2592.
32. Belardetti, F., and Siegelbaum, S. A. (1988) TINS 11, 232-238.
33. Belardetti, F., Campbell, W. B., Falck, J. R., Demontis, G., and Rosolowsky, M. (1989) Neuron 3, 497-505.
34. Pace-Asciak, C. R., and Martin, J. M. (1984) Prostagl Leukotriene and Med. 16, 173-180.
35. Pace-Asciak, C. R., Demin, P. M., Estrada, M., and Liu, G.-Y. (1999) FEBS Lett. 461, 165-168.
36. Demin, P. M., and Pace-Asciak, C. R. (1993) Tetrahedron Left. 34, 4305-4308.
37. Pace-Asciak, C. R., Hahn, S., Diamandis, E. P., Soleas, G., and Goldberg, D. M. (1995) Clin. Chim. Acta 235, 207-219.

38. Demin, P., Reynaud, D., and Pace-Asciak, C. R. (1995) *Anal. Biochem.* 226, 252-255.
39. Pace-Asciak, C. R., Klein, J., and Spielberg, S. P. (1986) *Biochim. Biophys. Acta* 875, 406-409.
40. Hishinuma, T., Yamazaki, T., and Mizugaki, M. (2000) *Prostaglandins & other Lipid Mediators* 62, 135-143.
41. Gorman, R. R., Bundy, G. L., Peterson, D. C., Sun, F. F., Miller, O. V., and Fitzpatrick, F. A. (1977) *Proc. Natl. Acad. Sci. USA* 74, 4007-4011.
42. Urban, M. (2000), *Orthopedics,* 23, S 7614.
43. Everts et al., (2000), *Clin. Rheumatol.,* 19, 33143.
44. Demin et al., (1995), *J. Chromatog. B.,* 672, 282-289.
45. Demin, P., Reynaud, D. and Pace-Asciak, C. R., (in press).
46. Pace-Asciak et al., (2000), Adv. Prostagl. and Leuk. Res., 11th. International Conference, Florence, Italy, June 4-8, Abstr. pp. 18.

We claim:

1. A method for selectively inhibiting thromboxane formation in a mammal comprising administering to the mammal an effective amount of a hepoxilin analog of the formula:

(I)

wherein X is $CH_2$;
R[1] is —$CH_2CH$=$CH$—$(CH_2)_3$—COR" wherein R" is OH, or O— lower alkyl;
R[2] is OH, and
R[3] is
—$CH_2$—$CH$=$CH$—$(CH_2)_4$—R'" wherein R'" is $CH_2OH$,
$CH_2$—O— lower alkyl or $CH_3$,
or

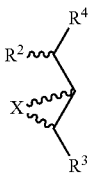

(II)

wherein X, R[2] and R[3] are as defined for formula I and R[4] is
—CH=CH—$CH_2$—CH=CH—$(CH_2)_3$—COR"
wherein R"=OH or O— lower alkyl, or of a sugar amide or sugar ester thereof;
wherein said analog is administered in a concentration that inhibits thromboxane formation in the absence of inhibition of phospholipase $A_2$.

2. A method for selectively inhibiting thromboxane formation in a mammal comprising administering to the mammal an effective amount of a compound selected from the group consisting of:
(a) 8(S)-hydroxy-11,12-cyclopropyl-eicosa-5Z,9E,14Z-trienoic acid or a sugar amide or sugar ester thereof;
(b) 8(R)-hydroxy-11,12-cyclopropyl-eicosa-5Z,9E,14Z-trienoic acid or a sugar amide or sugar ester thereof;
(c) 10(S)-hydroxy-11,12-cyclopropyl-eicosa-5Z,8Z,14Z-trienoic acid or a sugar amide or sugar ester thereof; and
(d) 10(R)-hydroxy-11,12-cyclopropyl-eicosa-5Z,8Z,14Z-trienoic acid or a sugar amide or sugar ester thereof;
wherein said compound is administered in a concentration that inhibits thromboxane formation in the absence of inhibition of phospholipase $A_2$.

3. A method for directly antagonising thromboxane activity in a mammal comprising administering to the mammal an effective amount of a hepoxilin analog of the formula:

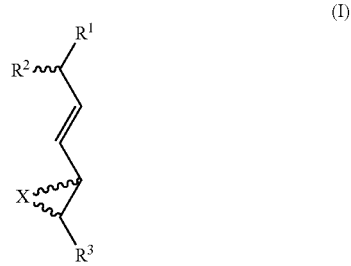

(I)

wherein X is $CH_2$;
R[1] is
—$CH_2CH$=$CH$—$(CH_2)_3$—COR" wherein R" is OH, or O— lower alkyl;
R[2] is OH; and
R[3] is
—$CH_2$—$CH$=$CH$—$(CH_2)_4$—R'" wherein R'" is $CH_2OH$,
$CH_2$—O— lower alkyl or $CH_3$,
or

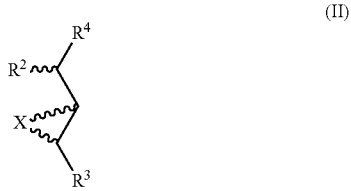

(II)

wherein X, R[2] and R[3] are as defined for formula I and R[4] is
CH=CH—$CH_2$—CH=CH—$(CH_2)_3$—COR"
wherein R"=OH or O— lower alkyl, or of a sugar amide or sugar ester thereof,
wherein said analog is administered in a concentration that directly antagonizes the thromboxane (TP) receptor.

4. A method for directly antagonising thromboxane activity in a mammal comprising administering to the mammal an effective amount of a compound selected from the group consisting of:
(a) 8(S)-hydroxy-11,12-cyclopropyl-eicosa-5Z,9E,14Z-trienoic acid or a sugar amide or sugar ester thereof;
(b) 8(R)-hydroxy-11,12-cyclopropyl-eicosa-5Z,9E,14Z-trienoic acid or a sugar amide or sugar ester thereof;
(c) 10(S)-hydroxy-11,12-cyclopropyl-eicosa-5Z,8Z,14Z-trienoic acid or a sugar amide or sugar ester thereof; and
(d) 10(R)-hydroxy-11,12-cyclopropyl-eicosa-5Z,8Z,14Z-trienoic acid or a sugar amide or sugar ester thereof;
wherein said compound is administered in a concentration that directly antagonizes the thromboxane (TP) receptor.

5. The method of claim 1, wherein said analog is administered in a concentration that additionally directly antagonizes the thromboxane (TP) receptor without substantially affecting thromboxane synthase.

6. The method of claim 2, wherein said compound is administered in a concentration that additionally directly antagonizes the thromboxane (TP) receptor without substantially affecting thromboxane synthase.

7. The method of claim 1, wherein said mammal suffers from a thromboxane-mediated disease.

8. The method of claim 1, wherein said mammal suffers from a disease selected from the group consisting of cardiovascular disease, thrombosis, diabetes mellitus, septic shock, and an eye disease associated with ocular inflammation and/or increased intraocular pressure.

9. The method of claim 1, wherein said mammal suffers from an eye disease associated with ocular inflammation and/or increased intraocular pressure.

10. The method of claim 2, wherein said mammal suffers from a thromboxane-mediated disease.

11. The method of claim 2, wherein said mammal suffers from a disease selected from the group consisting of cardiovascular disease, thrombosis, diabetes mellitus, septic shock, and an eye disease associated with ocular inflammation and/or increased intraocular pressure.

12. The method of claim 2, wherein said mammal suffers from an eye disease associated with ocular inflammation and/or increased intraocular pressure.

13. The method of claim 3, wherein said mammal suffers from a thromboxane-mediated disease.

14. The method of claim 3, wherein said mammal suffers from a disease selected from the group consisting of cardiovascular disease, thrombosis, diabetes mellitus, septic shock, and an eye disease associated with ocular inflammation and/or increased intraocular pressure.

15. The method of claim 3, wherein said mammal suffers from an eye disease associated with ocular inflammation and/or increased intraocular pressure.

16. The method of claim 4, wherein said mammal suffers from a thromboxane-mediated disease.

17. The method of claim 4, wherein said mammal suffers from a disease selected from the group consisting of cardiovascular disease, thrombosis, diabetes mellitus, septic shock, and an eye disease associated with ocular inflammation and/or increased intraocular pressure.

18. The method of claim 4, wherein said mammal suffers from an eye disease associated with ocular inflammation and/or increased intraocular pressure.

19. The method of claim 1, wherein said mammal suffers from thrombosis.

20. The method of claim 2, wherein said mammal suffers from thrombosis.

21. The method of claim 3, wherein said mammal suffers from thrombosis.

22. The method of claim 4, wherein said mammal suffers from thrombosis.

23. The method of claim 1, wherein the hepoxilin analog is administered at a concentration of up to 40 mg/kg.

24. The method of claim 2, wherein the hepoxilin analog is administered at a concentration of up to 40 mg/kg.

* * * * *